(12) United States Patent
Ryu et al.

(10) Patent No.: US 9,739,772 B2
(45) Date of Patent: Aug. 22, 2017

(54) METHOD OF ANALYZING BINDING ASPECT OF MEMBRANE PROTEIN IN A LIVING CELL

(71) Applicant: POSTECH ACADEMY-INDUSTRY FOUNDATION, Gyeongsangbuk-do (KR)

(72) Inventors: Sung Ho Ryu, Gyeongsangbuk-do (KR); Dohyeon Kim, Seoul (KR); Nam Ki Lee, Gyeongsangbuk-do (KR); Dong Kyun Kim, Gyeongsangbuk-do (KR); Soyeon Park, Seoul (KR); Yonghoon Kwon, Seoul (KR); Kai Zhou, Gyeongsangbuk-do (KR)

(73) Assignee: Postech Academy-Industry Foundation, Gyeongsangbuk-Do (KR)

( * ) Notice: Subject to any disclaimer, the term of this patent is extended or adjusted under 35 U.S.C. 154(b) by 0 days.

(21) Appl. No.: 14/891,555

(22) PCT Filed: May 16, 2014

(86) PCT No.: PCT/KR2014/004426
§ 371 (c)(1),
(2) Date: Nov. 16, 2015

(87) PCT Pub. No.: WO2014/185752
PCT Pub. Date: Nov. 20, 2014

(65) Prior Publication Data
US 2016/0116468 A1    Apr. 28, 2016

Related U.S. Application Data

(63) Continuation of application No. PCT/KR2013/011002, filed on Nov. 29, 2013.

(30) Foreign Application Priority Data

May 16, 2013 (KR) .................... 10-2013-0056008
May 16, 2014 (KR) .................... 10-2014-0059027

(51) Int. Cl.
*G01N 33/554* (2006.01)
*G01N 33/557* (2006.01)

(52) U.S. Cl.
CPC ......... *G01N 33/557* (2013.01); *G01N 33/554* (2013.01)

(58) Field of Classification Search
None
See application file for complete search history.

(56) References Cited

PUBLICATIONS

Stewart et al. Biochem J 1991 vol. 275, p. 569-573.*
Daumas et al. Biophysical J. 2003 vol. 84, p. 356-366.*
Jin et al. Biophysical J. 2007 vol. 93, p. 1079-1088.*
Saxton Biophysical J. 1997 vol. 72, p. 1744-1753.*

* cited by examiner

*Primary Examiner* — Jacob Cheu
(74) *Attorney, Agent, or Firm* — Lathrop & Gage LLP

(57) ABSTRACT

The present invention relates to a method for analyzing the pattern of live intercellular membrane protein binding. The method for analyzing the pattern according to the present invention can analyze accurately, sensitively, quickly, and readily the binding pattern of a target membrane protein and a candidate substance to be specifically bound therewith without tagging to a ligand, and thus measure directly and accurately the position and quantitative information of the binding of the membrane protein and the target substance. Such effects make it possible to apply the method for various uses such as dissociation constant, mutant study, complex formation, and signal transduction. Moreover, it is expected to use the method for searching out undiscovered membrane proteins and target substances.

19 Claims, 19 Drawing Sheets

[FIG. 1]
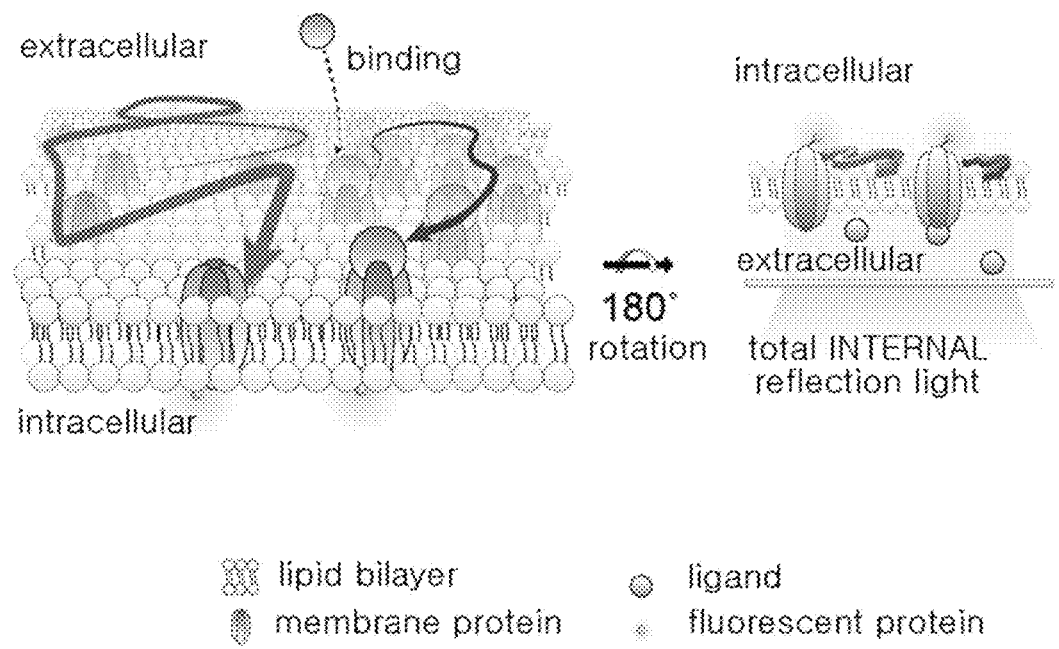
[FIG. 2]
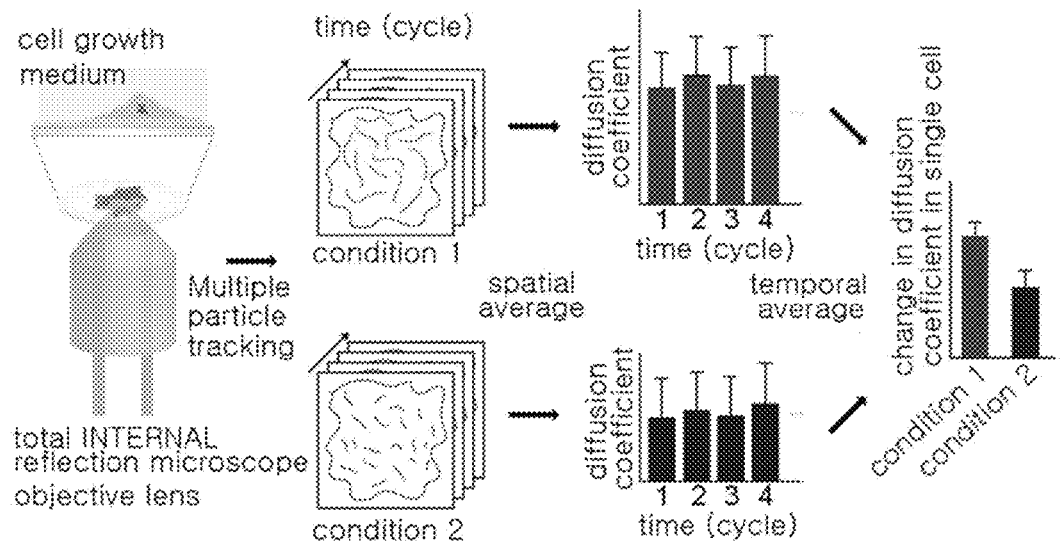

[FIG. 3]
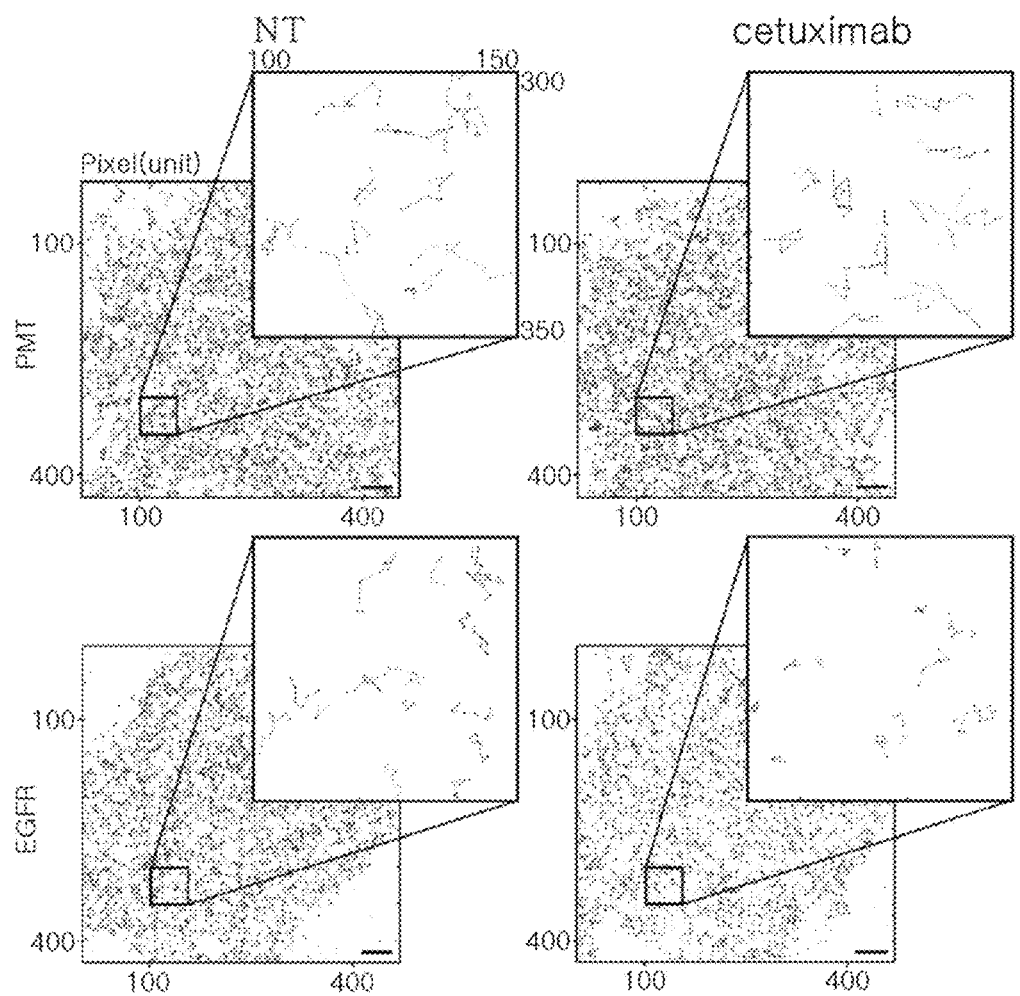

[FIG. 4]
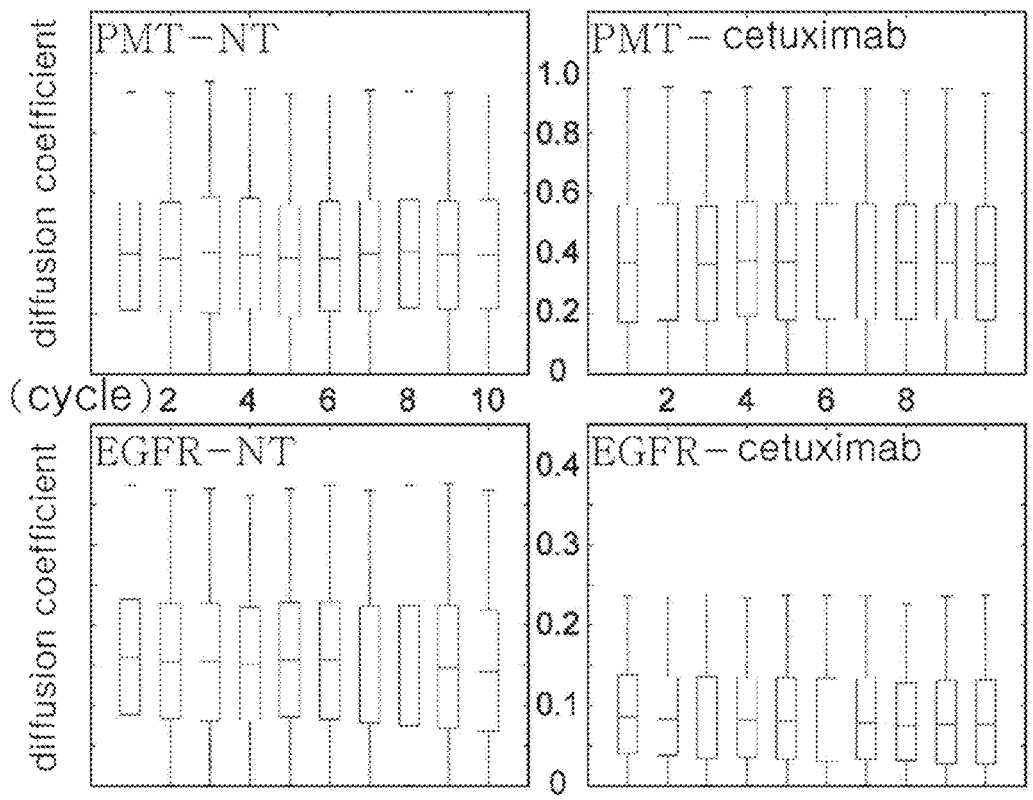
[FIG. 5]
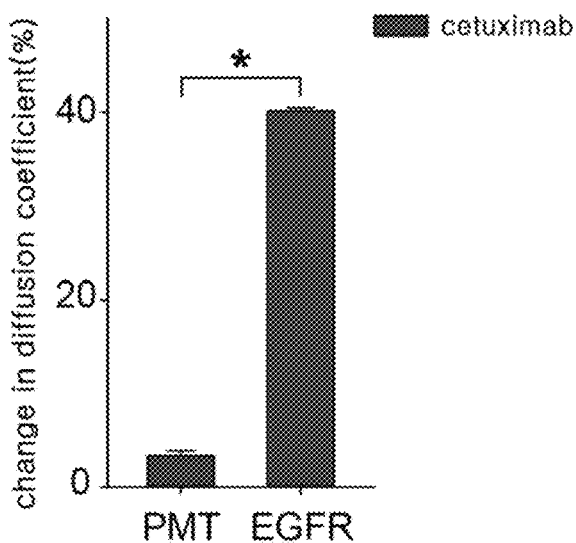

[FIG. 6]
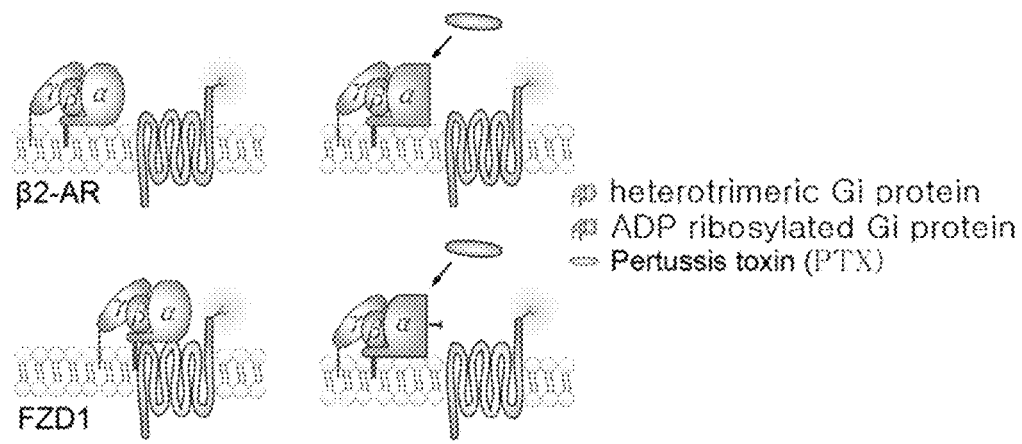
[FIG. 7]
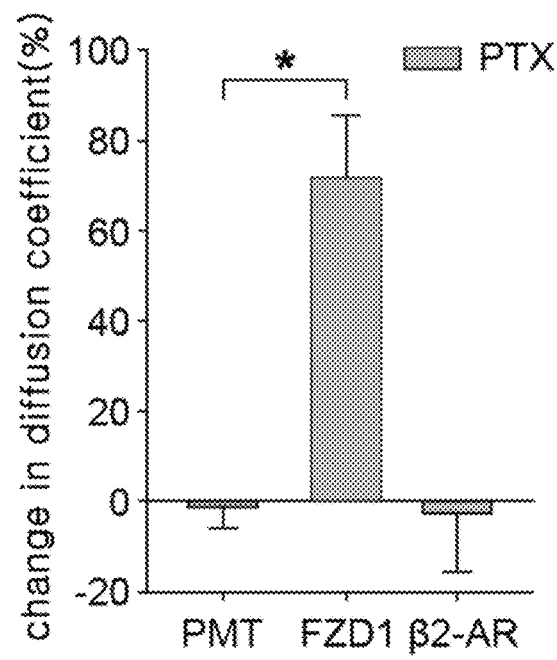

[FIG. 8]
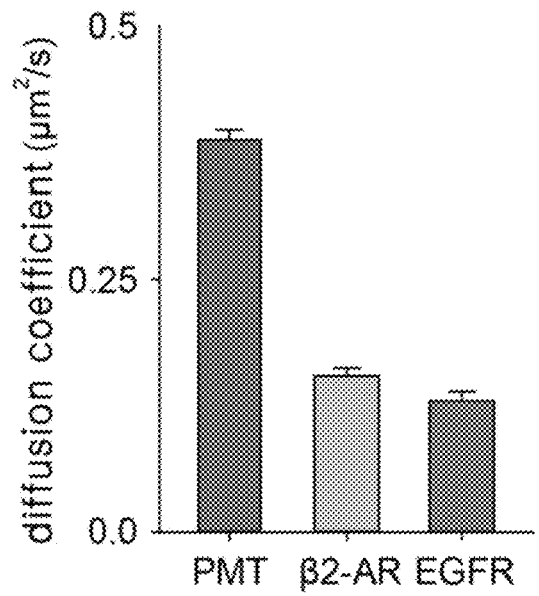
[FIG. 9]
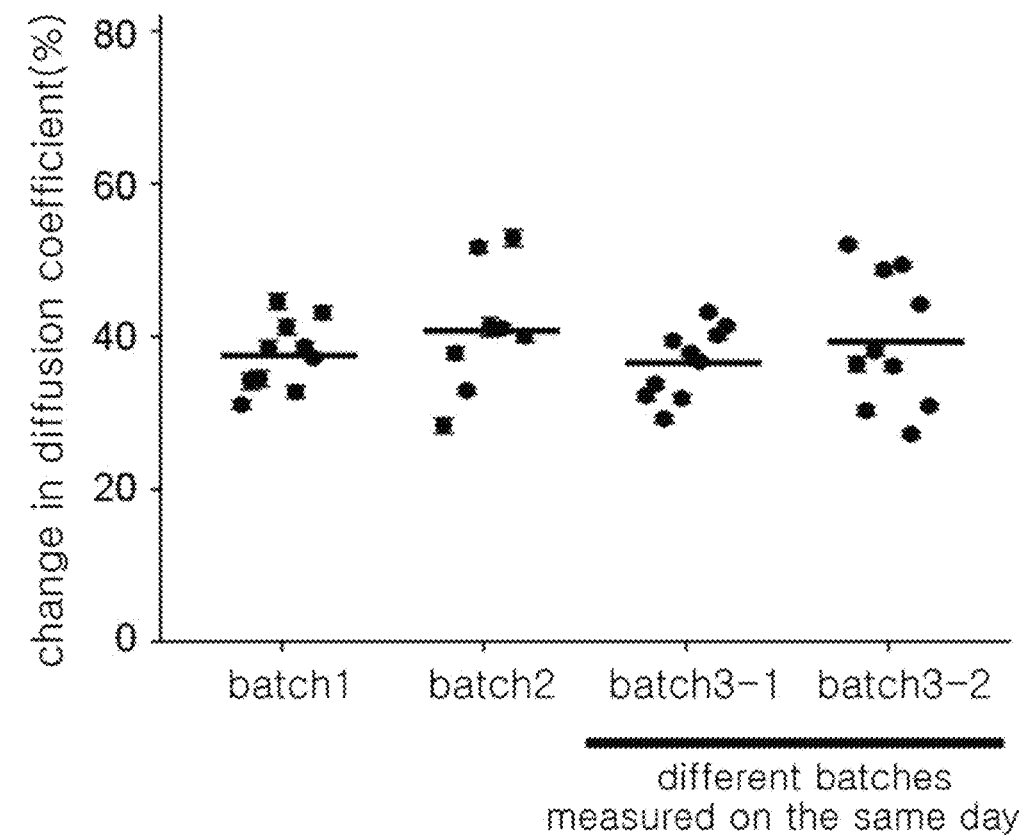

[FIG. 10]
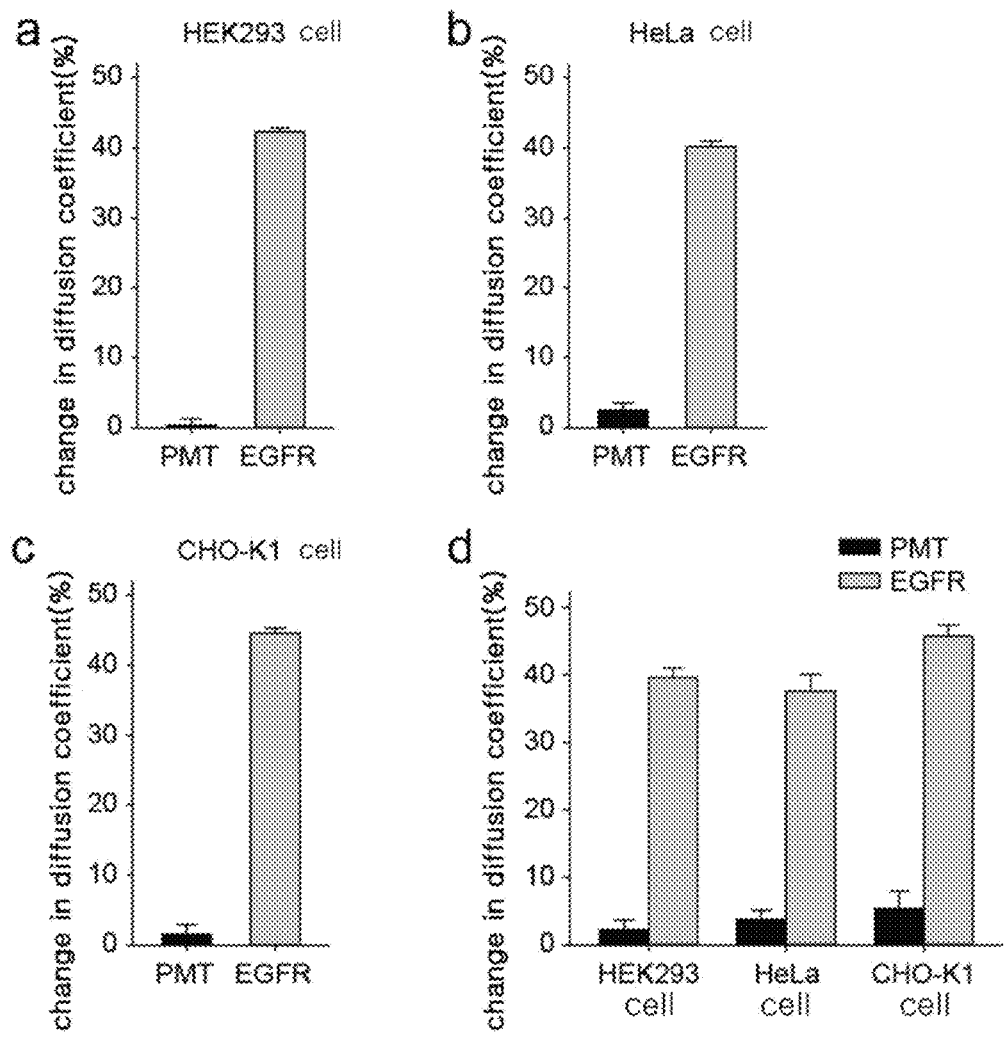
[FIG. 11]
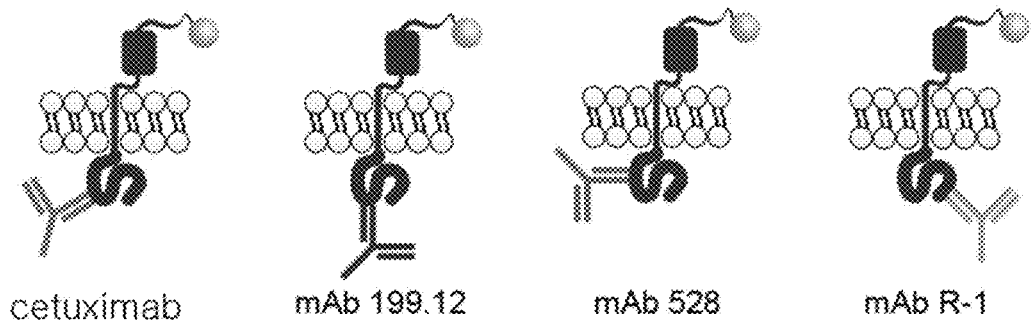
cetuximab     mAb 199.12     mAb 528     mAb R-1

[FIG. 12]
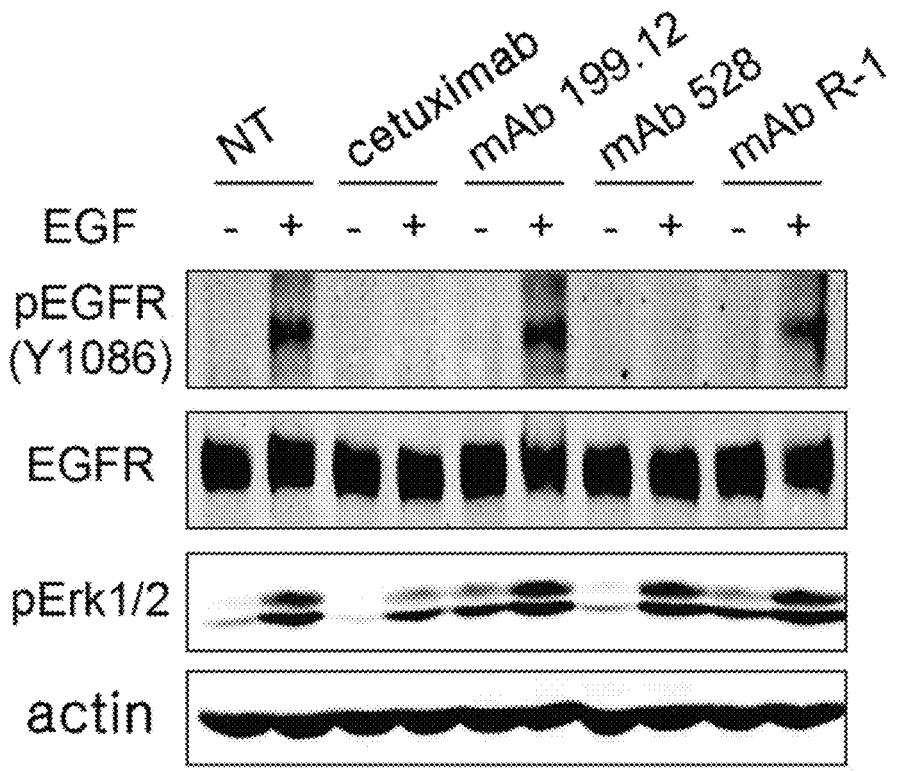
[FIG. 13]
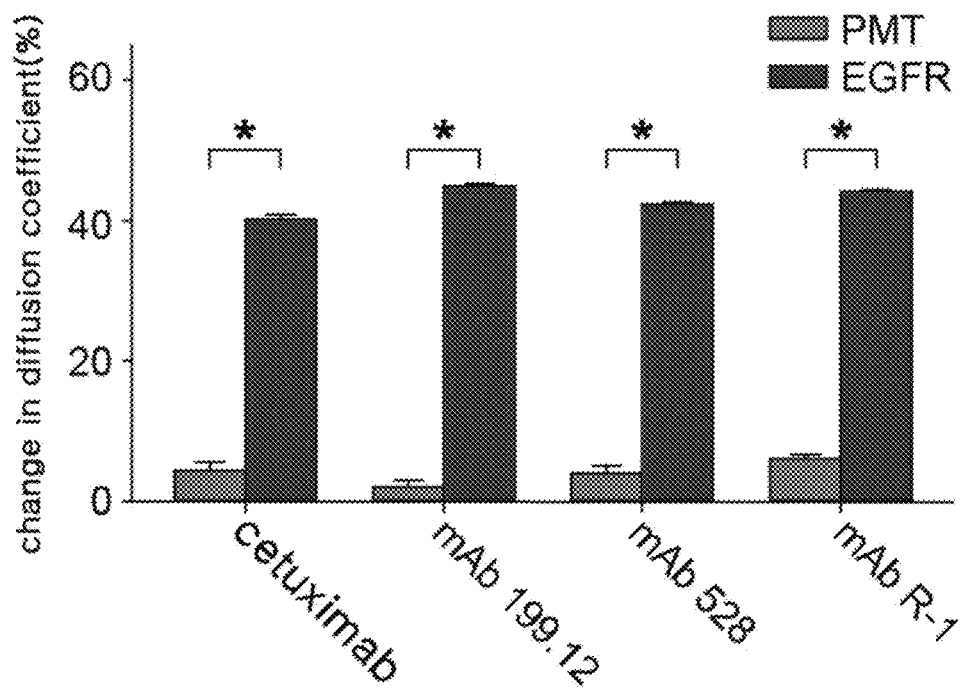

[FIG. 14]
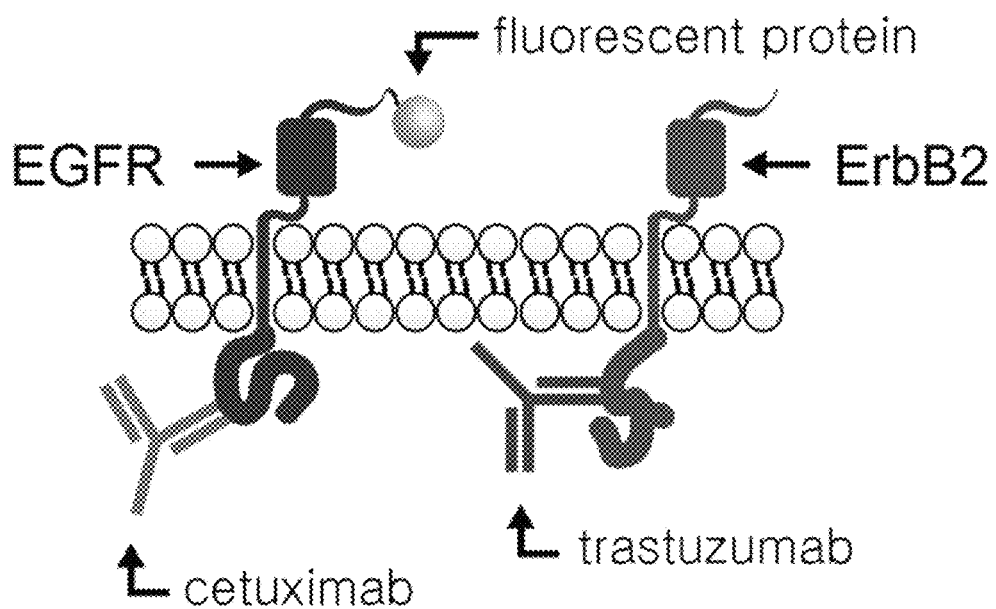
[FIG. 15]
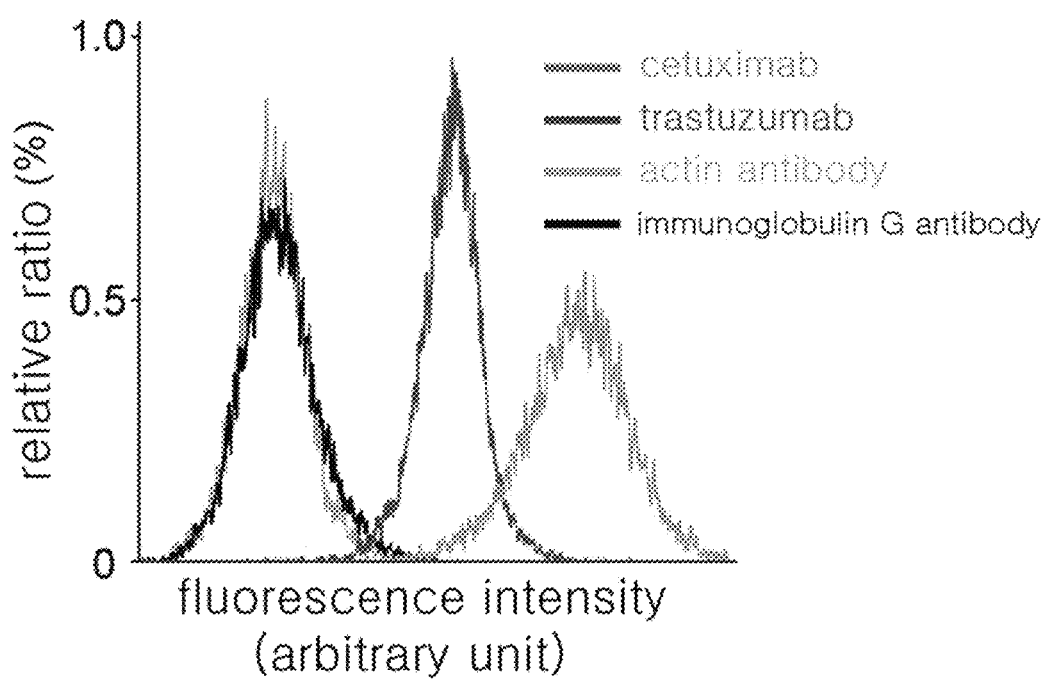

[FIG.16]
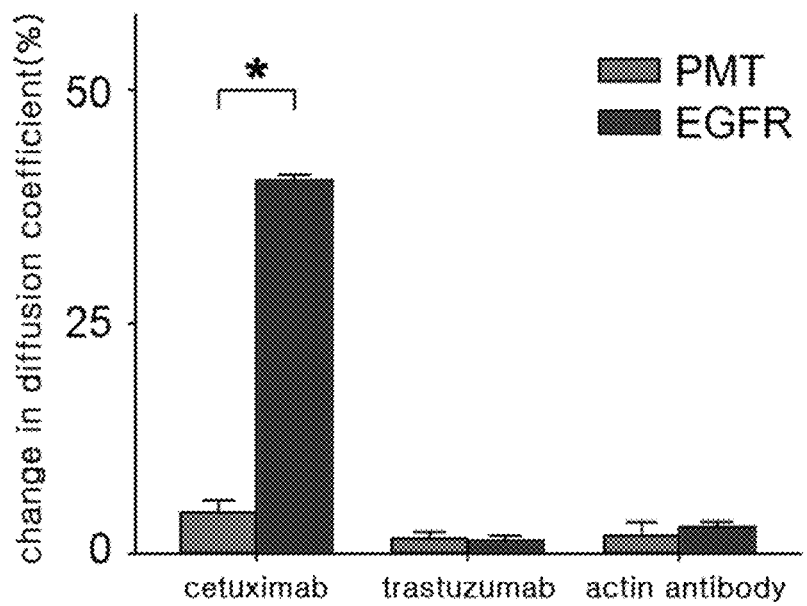
[FIG. 17]
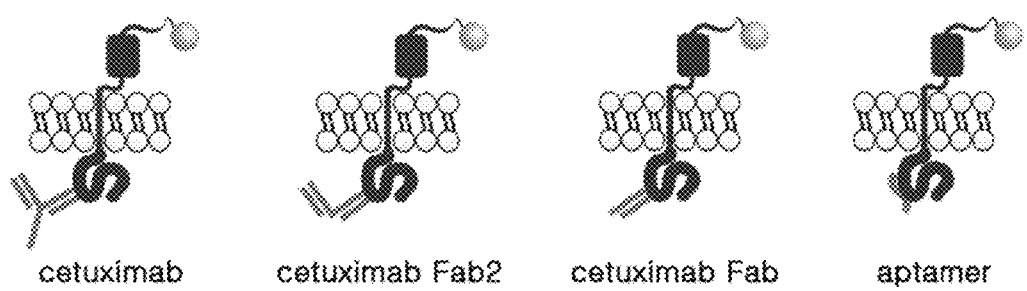
cetuximab     cetuximab Fab2     cetuximab Fab     aptamer

[FIG. 18]
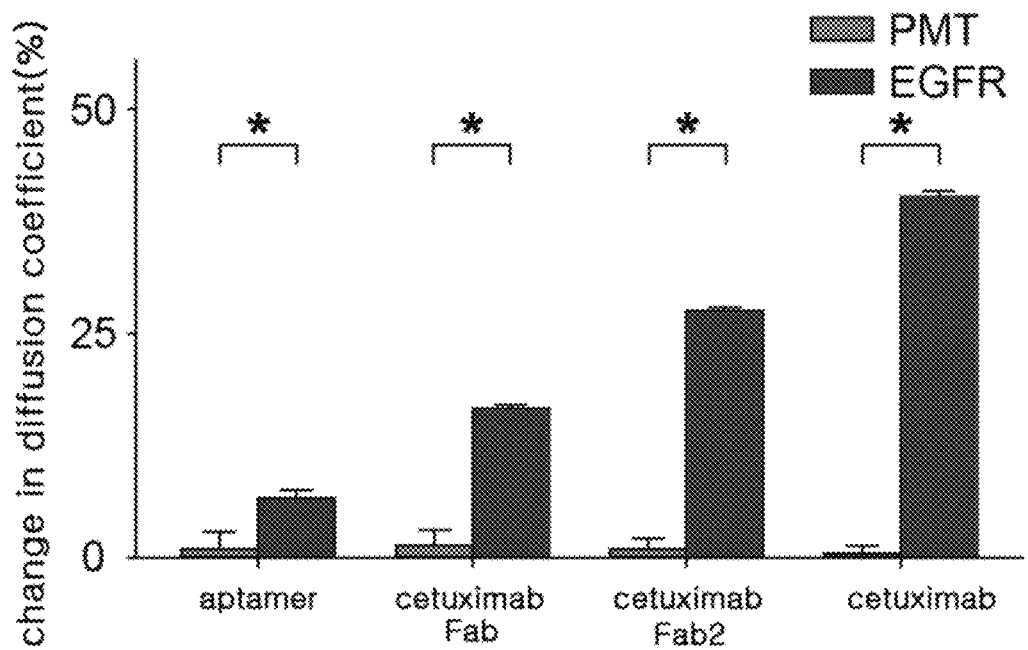
[FIG. 19]
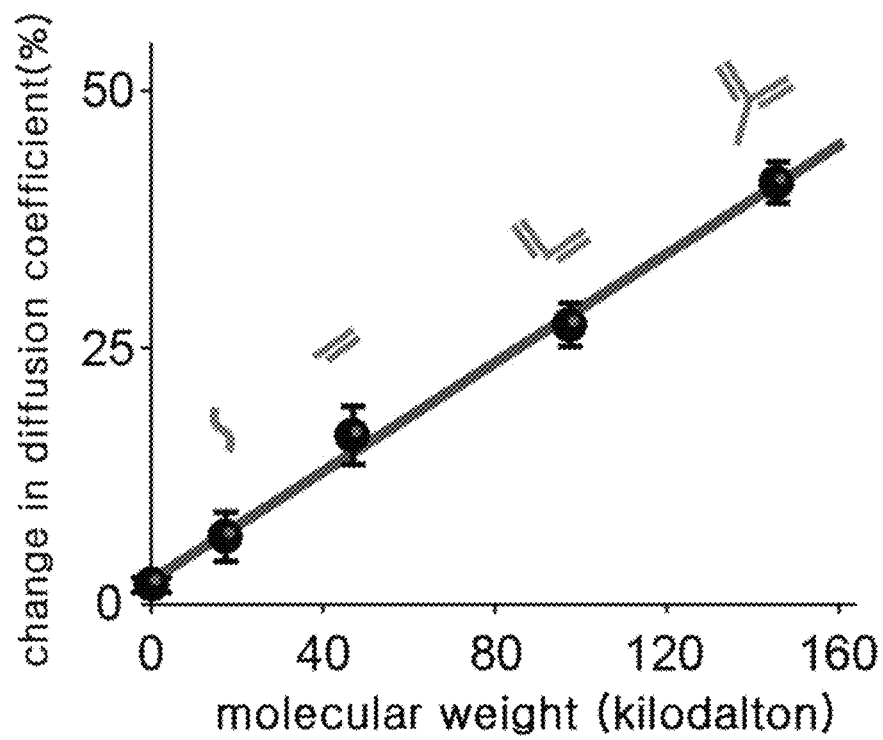

[FIG. 20]
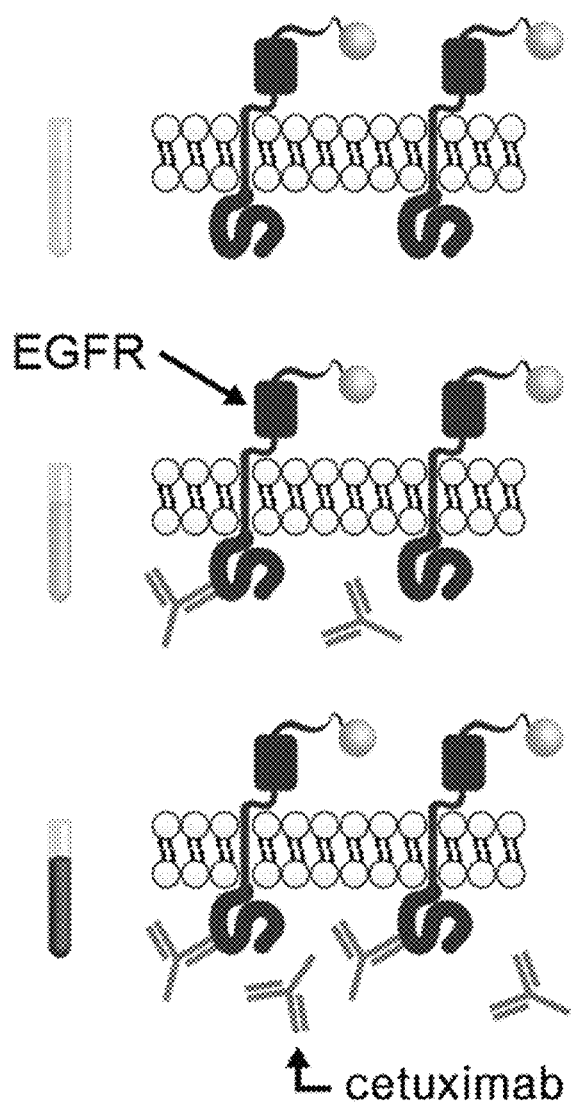

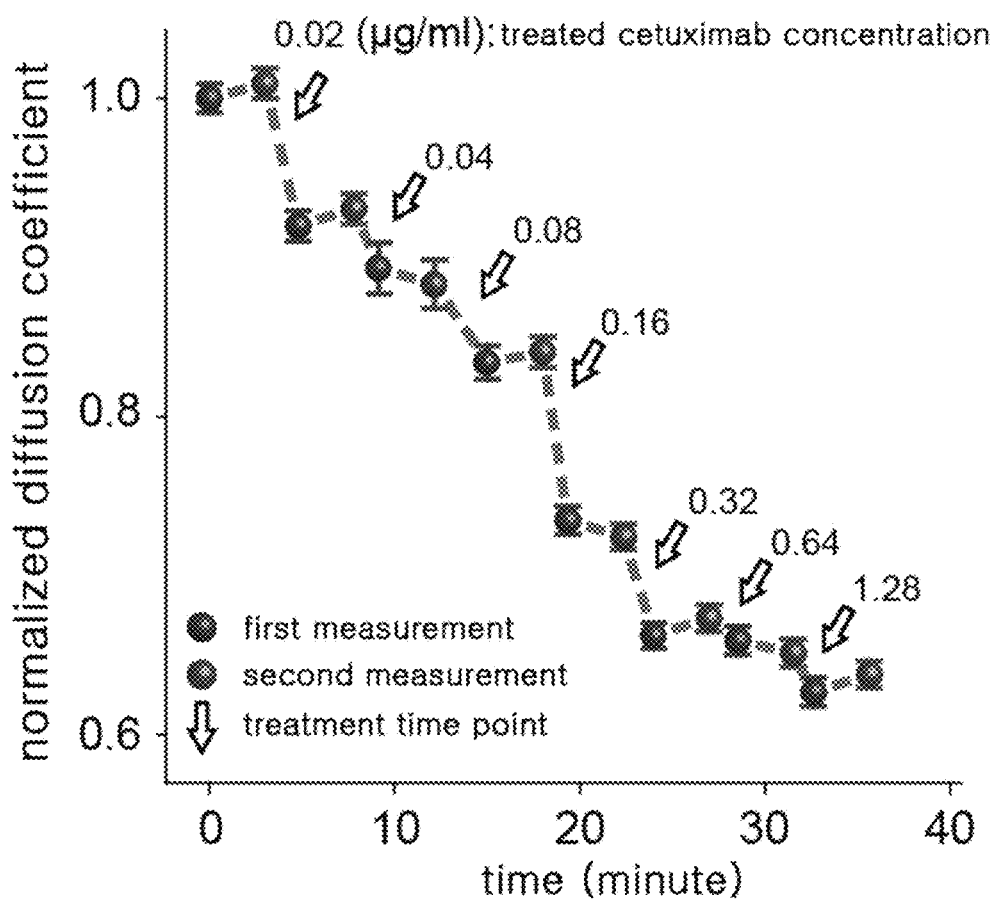
[FIG. 21]

[FIG. 22]
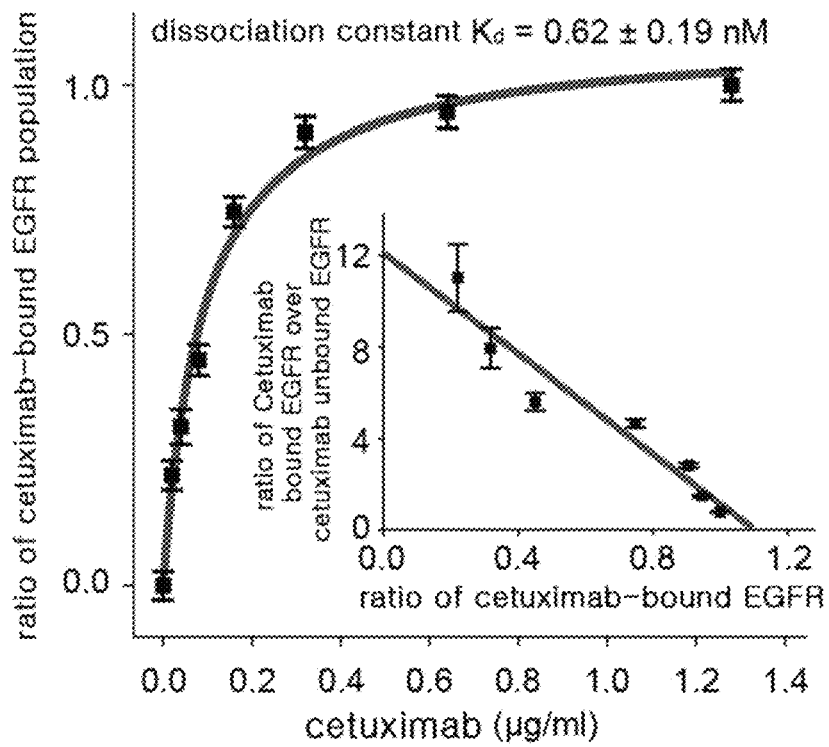
[FIG. 23]
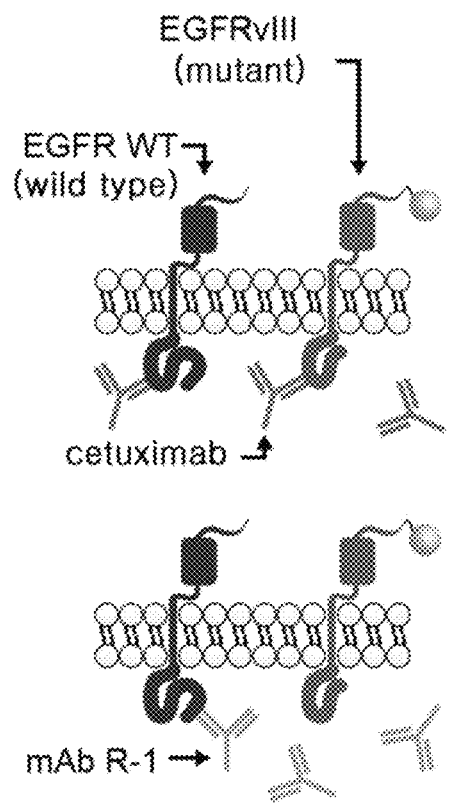

[FIG. 24]
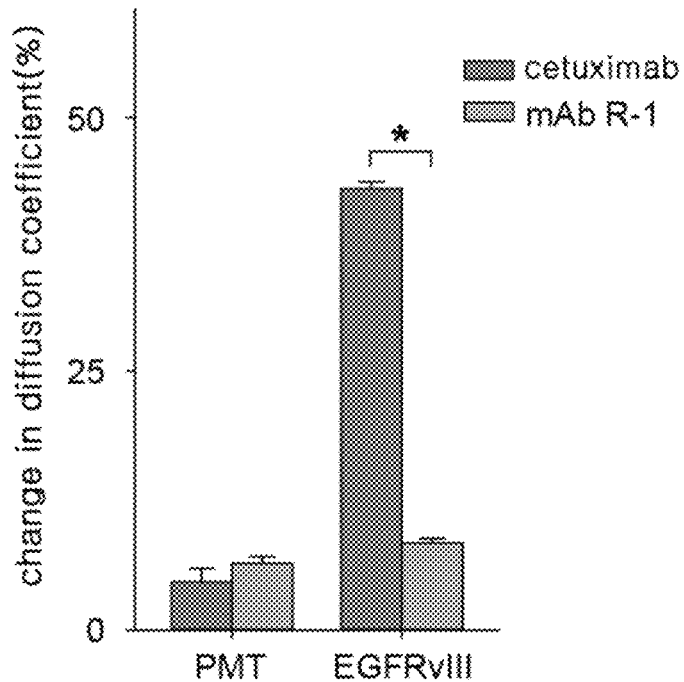
[FIG. 25]
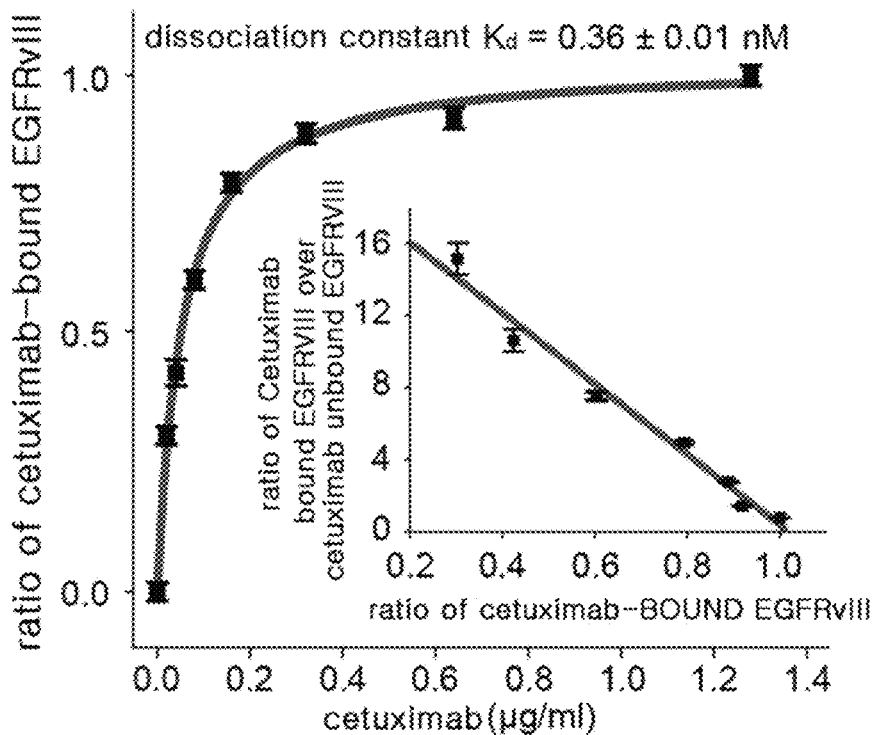

[FIG. 26]
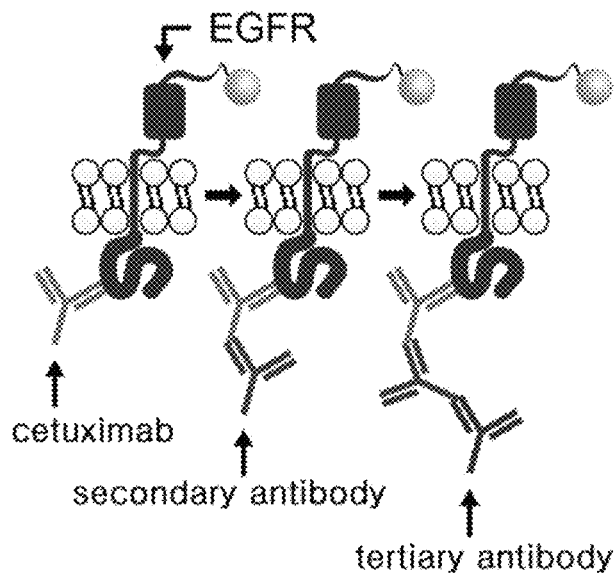
[FIG. 27]
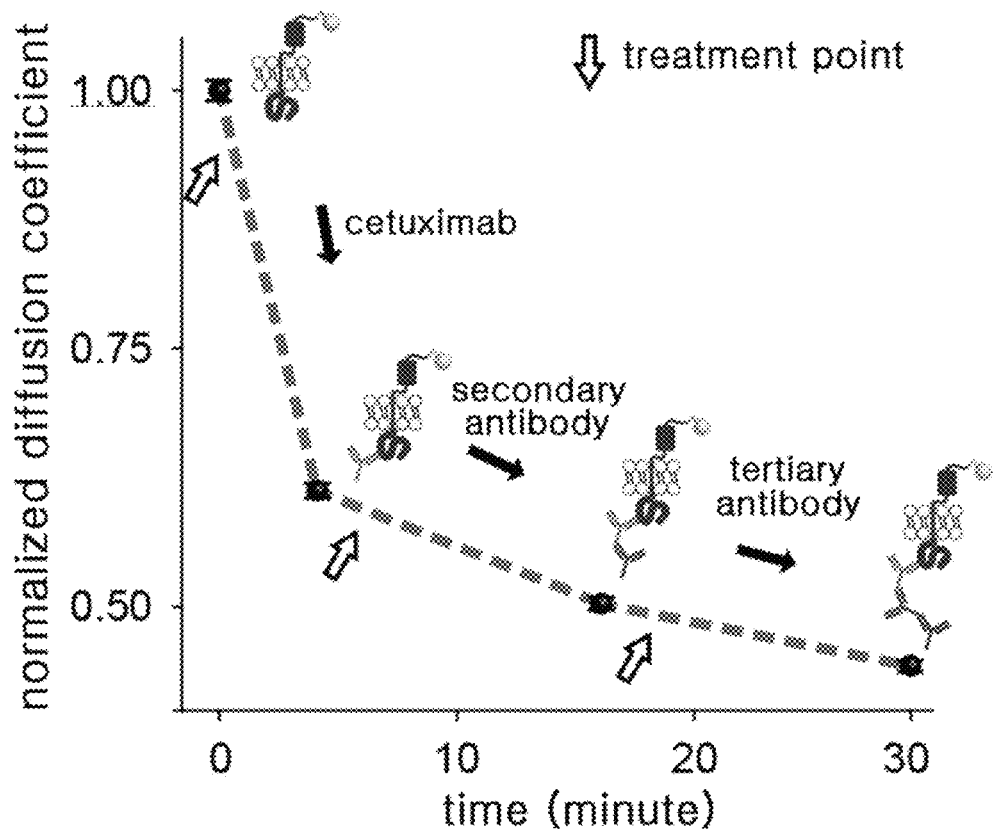

[FIG. 28]
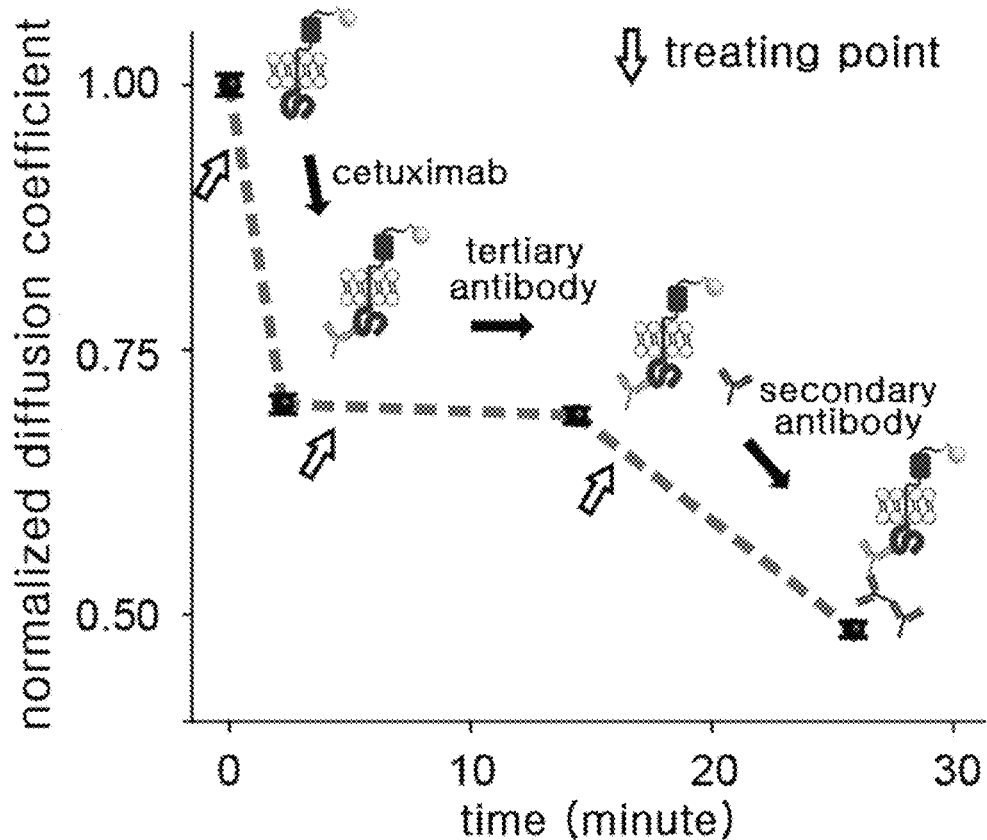
[FIG. 29]
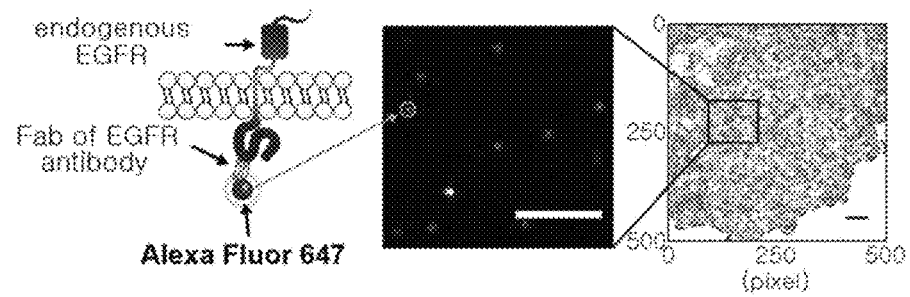

[FIG. 30]
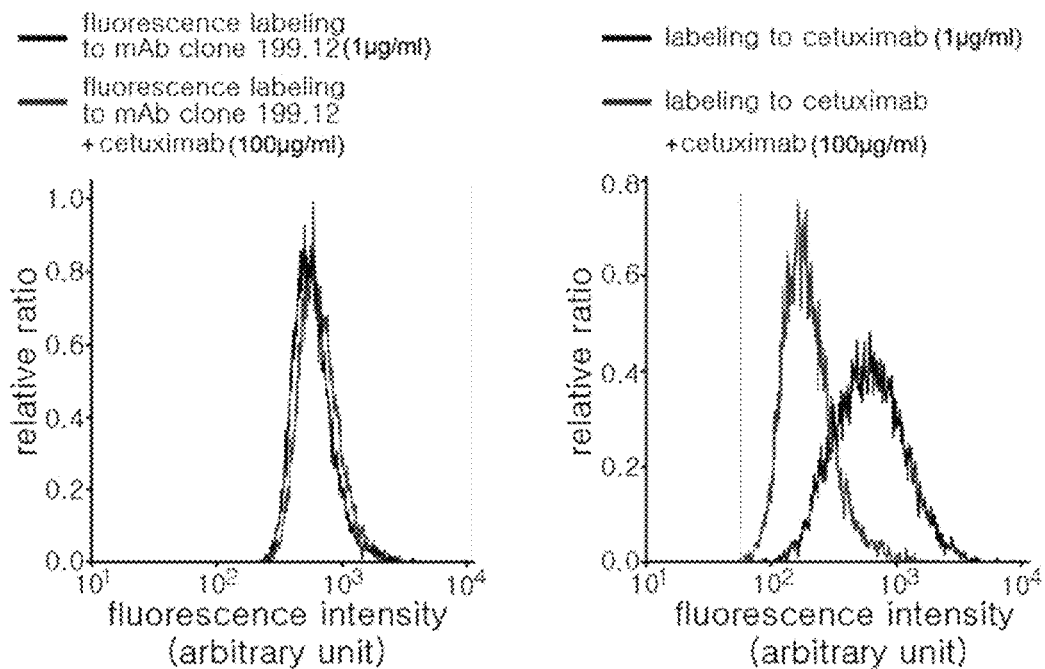
[FIG. 31]
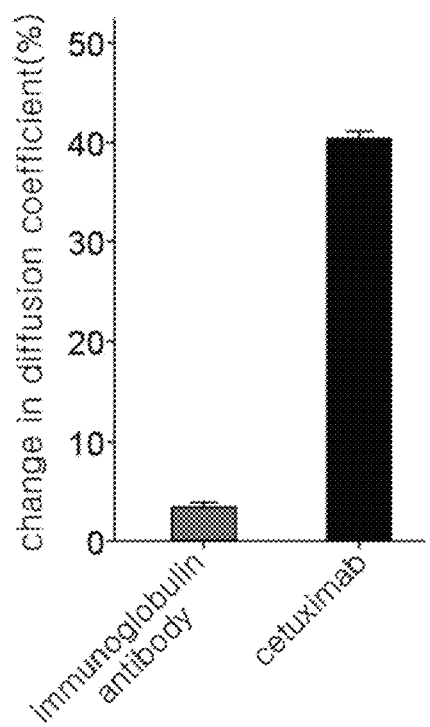

[FIG. 32]
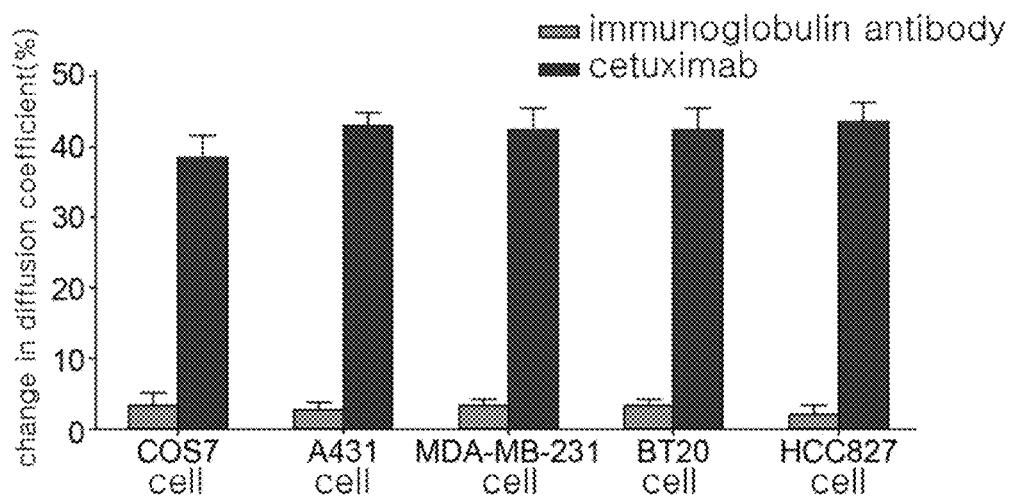
[FIG. 33]
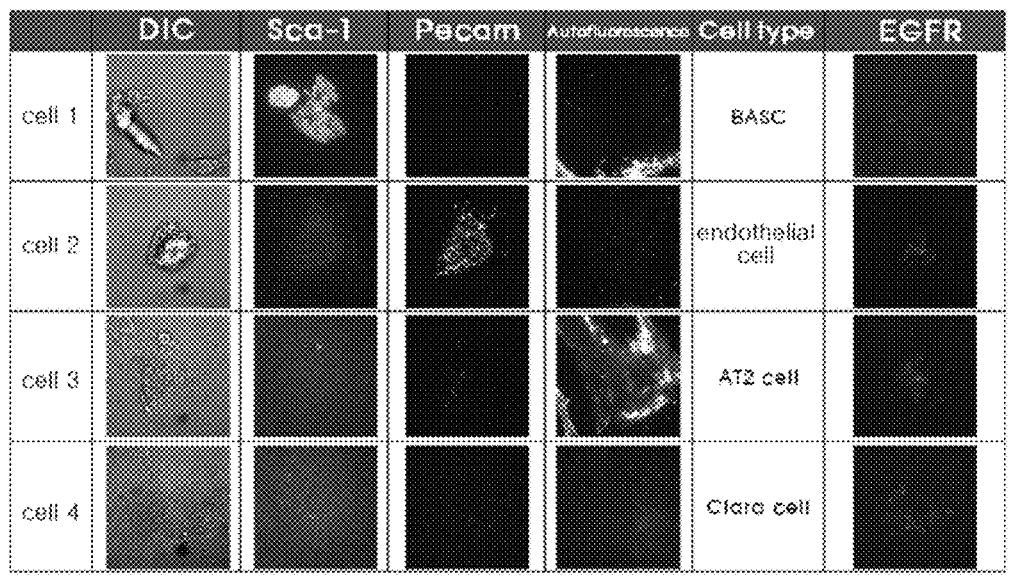

[FIG. 34]
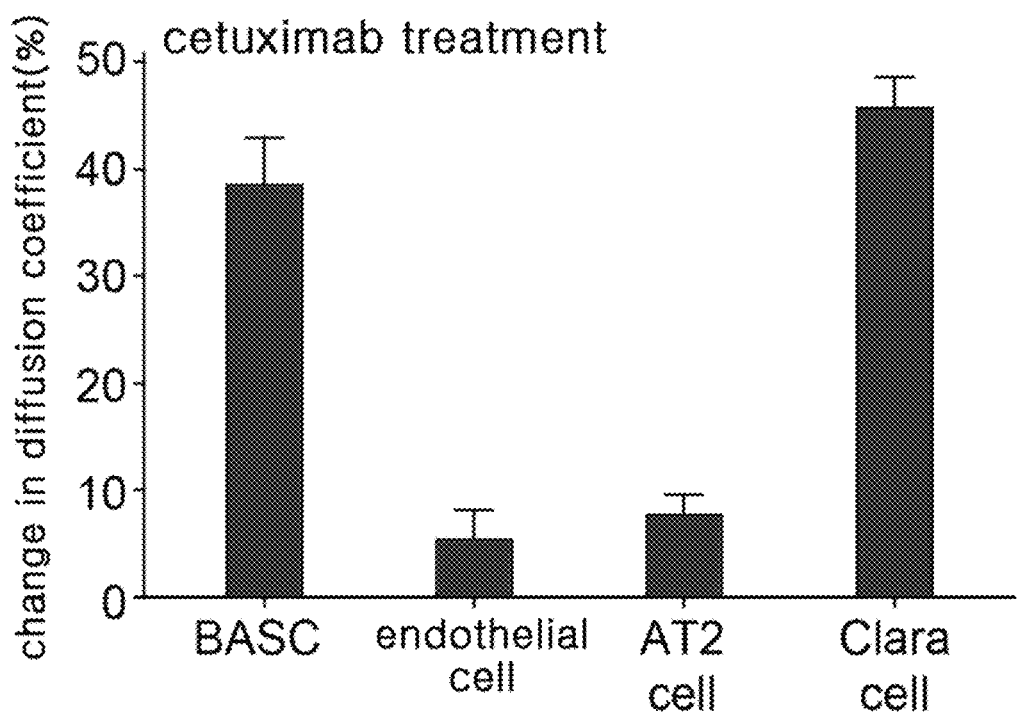

SEQUENCE LISTING

<160> NUMBER OF SEQ ID NOS: 8

<210> SEQ ID NO 1
<211> LENGTH: 3630
<212> TYPE: DNA
<213> ORGANISM: Homo sapiens

<400> SEQUENCE: 1

```
atgcgaccct ccgggacggc cggggcagcg ctcctggcgc tgctggctgc gctctgcccg      60
gcgagtcggg ctctggagga aaagaaagtt tgccaaggca cgagtaacaa gctcacgcag     120
ttgggcactt ttgaagatca ttttctcagc ctccagagga tgttcaataa ctgtgaggtg     180
gtccttggga atttggaaat tacctatgtg cagaggaatt atgatctttc cttcttaaag     240
accatccagg aggtggctgg ttatgtcctc attgccctca acacagtgga gcgaattcct     300
ttggaaaacc tgcagatcat cagaggaaat atgtactacg aaaattccta tgccttagca     360
gtcttatcta actatgatgc aaataaaacc ggactgaagg agctgcccat gagaaattta     420
caggaaatcc tgcatggcgc cgtgcggttc agcaacaacc ctgccctgtg caacgtggag     480
agcatccagt ggcgggacat agtcagcagt gactttctca gcaacatgtc gatggacttc     540
cagaaccacc tgggcagctg ccaaaagtgt gatccaagct gtcccaatgg gagctgctgg     600
ggtgcaggag aggagaactg ccagaaactg accaaaatca tctgtgccca gcagtgctcc     660
gggcgctgcc gtggcaagtc ccccagtgac tgctgccaca accagtgtgc tgcaggctgc     720
acaggccccc gggagagcga ctgcctggtc tgccgcaaat tccgagacga agccacgtgc     780
aaggacacct gccccccact catgctctac aaccccacca cgtaccagat ggatgtgaac     840
cccgagggca atacagcttt ggtgccacct cgcgtgaaga gtgtccccg taattatgtg     900 gtgacagatc acggctcgtg cgtccgagcc tgtgggccg acagctatga gatggaggaa     960
gacggcgtcc gcaagtgtaa gaagtgcgaa gggccttgcc gcaaagtgtg taacggaata    1020
ggtattggtg aatttaaaga ctcactctcc ataaatgcta cgaatattaa acacttcaaa    1080
aactgcacct ccatcagtgg cgatctccac atcctgccgg tggcatttag gggtgactcc    1140
ttcacacata tcctcctctc tggatccacag gaactggata ttctgaaaac cgtaaaggaa    1200
atcacagggt ttttgctgat tcaggcttgg cctgaaaaca ggacggacct ccatgccttt    1260
gagaacctag aaatcatacg cggcaggacc aagcaacatg gtcagttttc tcttgcagtc    1320
gtcagcctga acataacatc cttgggatta cgctccctca aggagataag tgatggagat    1380
gtgataattt caggaaacaa aaatttgtgc tatgcaaata acaataaactg gaaaaaactg    1440 tttgggacct ccggtcagaa aaccaaaatt ataagcaaca gaggtgaaaa cagctgcaag    1500
gccacaggcc aggtctgcca tgccttgtgc tccccgagg ctgctgggg ccggagccc     1560 agggactgcg tctcttgccg gaatgtcagc cgaggcaggg aatgcgtgga caagtgcaac    1620
cttctggagg gtgagccaag ggagtttgtg gagaactctg agtgcataca gtgccaccca    1680
gagtgcctgc ctcaggccat gaacatcacc tgcacaggac gggaccaga caactgtatc    1740
```

| | |
|---|---|
| cagtgtgccc actacattga cggcccccac tgcgtcaaga cctgcccggc aggagtcatg | 1800 |
| ggagaaaaca acaccctggt ctggaagtac gcagacgccg ccatgtgtg ccacctgtgc | 1860 |
| catccaaact gcacctacgg atgcactggg ccaggtcttg aaggctgtcc aacgaatggg | 1920 |
| cctaagatcc cgtccatcgc cactgggatg gtggggggccc tcctcttgct gctggtggtg | 1980 |
| gccctgggga tcggcctctt catgcgaagg cgccacatcg ttcggaagcg cacgctgcgg | 2040 |
| aggctgctgc aggagaggga gcttgtggag cctcttacac ccagtggaga agctcccaac | 2100 |
| caagctctct tgaggatctt gaaggaaact gaattcaaaa agatcaaagt gctgggctcc | 2160 |
| ggtgcgttcg gcacggtgta taagggactc tggatcccag aaggtgagaa agttaaaatt | 2220 |
| cccgtcgcta tcaaggaatt aagagaagca acatctccga aagccaacaa ggaaatcctc | 2280 |
| gatgaagcct acgtgatggc cagcgtggac aaccccacg tgtgccgcct gctgggcatc | 2340 |
| tgcctcacct ccaccgtgca gctcatcacg cagctcatgc ccttcggctg cctcctggac | 2400 |
| tatgtccggg aacacaaaga caatattggc tcccagtacc tgctcaactg gtgtgtgcag | 2460 |
| atcgcaaagg gcatgaacta cttggaggac cgtcgcttgg tgcaccgcga cctggcagcc | 2520 |
| aggaacgtac tggtgaaaac accgcagcat gtcaagatca cagattttgg gctggccaaa | 2580 |
| ctgctgggtg cggaagagaa agaataccat gcagaaggag gcaaagtgcc tatcaagtgg | 2640 |
| atggcattgg aatcaattt acacagaatc tatacccacc agagtgatgt ctggagctac | 2700 |
| ggggtgaccg tttgggagtt gatgaccttt ggatccaagc catatgacgg aatccctgcc | 2760 |
| agcgagatct cctccatcct ggagaaagga gaacgcctcc ctcagccacc catatgtacc | 2820 |
| atcgatgtct acatgatcat ggtcaagtgc tggatgatag acgcagatag tcgcccaaag | 2880 |
| ttccgtgagt tgatcatcga attctccaaa atggcccgag accccagcg ctaccttgtc | 2940 |
| attcaggggg atgaaagaat gcatttgcca agtcctacag actccaactt ctaccgtgcc | 3000 |
| ctgatggatg aagaagacat ggacgacgtg gtggatgccg acgagtacct catcccacag | 3060 |
| cagggcttct tcagcagccc ctccacgtca cggactcccc tcctgagctc tctgagtgca | 3120 |
| accagcaaca attccaccgt ggcttgcatt gatagaaatg ggctgcaaag ctgtcccatc | 3180 |
| aaggaagaca gcttcttgca gcgatacagc tcagacccca caggcgcctt gactgaggac | 3240 |
| agcatagacg acaccttcct cccagtgcct gaatacataa accagtccgt tcccaaaagg | 3300 |
| cccgctggct ctgtgcagaa tcctgtctat cacaatcagc ctctgaaccc cgcgcccagc | 3360 |
| agagacccac actaccagga ccccacagc actgcagtgg gcaaccccga gtatctcaac | 3420 |
| actgtccagc ccacctgtgt caacagcaca ttcgacagcc ctgcccactg ggcccagaaa | 3480 |
| ggcagccacc aaattagcct ggacaaccct gactaccagc aggacttctt tcccaaggaa | 3540 |
| gccaagccaa atggcatctt taagggctcc acagctgaaa atgcagaata cctaagggtc | 3600 |
| gcgccacaaa gcagtgaatt tattggagca | 3630 |

<210> SEQ ID NO 2
<211> LENGTH: 678
<212> TYPE: DNA
<213> ORGANISM: Artificial Sequence
<220> FEATURE:
<223> OTHER INFORMATION: mEos3.2

<400> SEQUENCE: 2

| | |
|---|---|
| atgagtgcga ttaagccaga catgaagatc aaactccgta tggaaggcaa cgtaaacggg | 60 |
| caccactttg tgatcgacgg agatggtaca ggcaagcctt ttgagggaaa acagagtatg | 120 |
| gatcttgaag tcaaagaggg cggacctctg ccttttgcct ttgatatcct gaccactgca | 180 |

-continued

```
ttccattacg gcaacagggt attcgccaaa tatccagaca acatacaaga ctattttaag      240
cagtcgtttc ctaaggggta ttcgtgggaa cgaagcttga ctttcgaaga cgggggcatt      300
tgcaacgcca gaaacgacat aacaatggaa ggggacactt tctataataa agttcgattt      360
tatggtacca actttcccgc caatggtcca gttatgcaga agaagacgct gaaatgggag      420
ccctccactg agaaaatgta tgtgcgtgat ggagtgctga cgggtgatat tgagatggct      480
ttgttgcttg aaggaaatgc ccattaccga tgtgacttca gaactactta caaagctaag      540
gagaagggtg tcaagttacc aggcgcccac tttgtggacc actgcattga gattttaagc      600
catgacaaag attacaacaa ggttaagctg tatgagcatg ctgttgctca ttctggattg      660
cctgacaatg ccagacga                                                    678
```

<210> SEQ ID NO 3
<211> LENGTH: 6
<212> TYPE: DNA
<213> ORGANISM: Artificial sequence
<220> FEATURE:
<223> OTHER INFORMATION: XbaI restriction site

<400> SEQUENCE: 3

```
tctaga                                                                   6
```

<210> SEQ ID NO 4
<211> LENGTH: 8
<212> TYPE: DNA
<213> ORGANISM: Artificial Sequence
<220> FEATURE:
<223> OTHER INFORMATION: NotI restriction site

<400> SEQUENCE: 4

```
gcggccgc                                                                 8
```

<210> SEQ ID NO 5
<211> LENGTH: 45
<212> TYPE: DNA
<213> ORGANISM: Homo sapiens

<400> SEQUENCE: 5

```
atgggctgct tcttcagcaa gcggcggaag gccgacaagg agagc                       45
```

<210> SEQ ID NO 6
<211> LENGTH: 1239
<212> TYPE: DNA
<213> ORGANISM: Homo sapiens

<400> SEQUENCE: 6

```
atggggcaac ccgggaacgg cagcgccttc ttgctggcac ccaatagaag ccatgcgccg       60
gaccacgacg tcacgcagca aagggacgag gtgtgggtgg tgggcatggg catcgtcatg      120
tctctcatcg tcctggccat cgtgtttggc aatgtgctgg tcatcacagc cattgccaag      180
ttcgagcgtc tgcagacggt caccaactac ttcatcactt cactggcctg tgctgatctg      240
gtcatgggcc tggcagtggt gcccttgggg gccgcccata ttcttatgaa aatgtggact      300
tttggcaact tctggtgcga gttttggact tccattgatg tgctgtgcgt cacggccagc      360
attgagaccc tgtgcgtgat cgcagtggat cgctactttg ccattacttc acctttcaag      420
taccagagcc tgctgaccaa gaataaggcc cgggtgatca ttctgatggt gtggattgtg      480
tcaggcctta cctccttctt gcccattcag atgcactggt accgggccac ccaccaggaa      540
```

| | |
|---|---:|
| gccatcaact gctatgccaa tgagacctgc tgtgacttct tcacgaacca agcctatgcc | 600 |
| attgcctctt ccatcgtgtc cttctacgtt ccccctggtga tcatggtctt cgtctactcc | 660 |
| agggtctttc aggaggccaa aaggcagctc cagaagattg acaaatctga gggccgcttc | 720 |
| catgtccaga accttagcca ggtggagcag gatgggcgga cggggcatgg actccgcaga | 780 |
| tcttccaagt tctgcttgaa ggagcacaaa gccctcaaga cgttaggcat catcatgggc | 840 |
| actttcaccc tctgctggct gcccttcttc atcgttaaca ttgtgcatgt gatccaggat | 900 |
| aacctcatcc gtaaggaagt ttacatcctc ctaaattgga taggctatgt caattctggt | 960 |
| ttcaatcccc ttatctactg ccggagccca gatttcagga ttgccttcca ggagcttctg | 1020 |
| tgcctgcgca ggtcttcttt gaaggcctat gggaatggct actccagcaa cggcaacaca | 1080 |
| ggggagcaga gtggatatca cgtggaacag gagaaagaaa ataaactgct gtgtgaagac | 1140 |
| ctcccaggca cggaagactt tgtgggccat caaggtactg tgcctagcga taacattgat | 1200 |
| tcacaaggga ggaattgtag tacaaatgac tcactgctg | 1239 |

<210> SEQ ID NO 7
<211> LENGTH: 1926
<212> TYPE: DNA
<213> ORGANISM: Rattus norvegicus

<400> SEQUENCE: 7

| | |
|---|---:|
| atggctgagg aggcggtgcc tagcgagtcc cgggccgccg gccggccgag cttggaacttt | 60 |
| tgtgccgtag cactccccgg ccggcgggag gaggtggggc accaggacac ggctggccac | 120 |
| cgccggcccc gggctgactc ccggtgctgg gctagagggc tactgctgct tctttggctg | 180 |
| ctggaggctc ctctgctttt gggggtccga gcgcaggcgg cgggccaggt atccgggccg | 240 |
| ggccagcaag ctccgccgcc gccccagcca cagcagggcg ggcagcagta caacggcgaa | 300 |
| cggggcatct ccatcccgga ccacggctac tgtcagccca tctccatccc gctgtgcacg | 360 |
| gacatcgcgt acaatcagac catcatgccc aacctgctgg ccacacgaa tcaggaggac | 420 |
| gccggcctgg aggtgcacca gttctacccg ttggtgaagg tgcagtgctc agccgagctc | 480 |
| aagttcttcc tgtgctccat gtacgcgcct gtgtgcaccg tactggagca ggcgctgccg | 540 |
| ccctgccgct ccctgtgcga gcgcgcgcgc cagggctgcg aggcactcat gaacaagttc | 600 |
| ggcttccagt ggccagacac gctcaagtgc gagaagttcc ctgtgcacgg cgcaggagag | 660 |
| ctgtgcgtgg gccagaacac ttccgacaaa ggcacccga ctccctcctt gctgccggag | 720 |
| ttctggacca gcaatccgca gcacggcggc ggtggttacc gcggcggcta cccgggaggt | 780 |
| gccggccccg tggagcgggg aaagttctcc tgcccgcgcg ccctcagggt gccttcctac | 840 |
| ctcaactatc actttctggg ggagaaggac tgcggcgcgc cctgcgaacc cactaaagta | 900 |
| tacgggctca tgtacttcgg gcctgaggag ttgcgctttt cgcgcacctg dataggcatc | 960 |
| tggtcggtgc tgtgctgcgc ctccacgctc ttcacggtgc tcacgtacct agtagacatg | 1020 |
| cggcgcttca gctaccgga gcggcccatt atttttcctgt ccggctgtta cacagcggtg | 1080 |
| gcggtggcct atatcgccgg ctttctgttg gaggaccggg tggtgtgcaa cgacaagttt | 1140 |
| gcagaggacg gggcgcgcac ggtggcgcag ggcactaaga aggaggggtg caccatcctc | 1200 |
| tttatgatgc tctacttctt cagcatggcc agctccatct ggtgggtaat cctgtccctc | 1260 |
| acctggttcc tggcagccgg catgaagtgg ggccacgaag ccatcgaggc caactcacaa | 1320 |
| tattttcacc tagccgcctg ggctgtacca gccattaaaa ctataaccat cctggcgctg | 1380 |
| ggccaagtgg atggcgacgt actgagtgga gtgtgttttg tggggctcaa taacgtggat | 1440 |

-continued

| | |
|---|---|
| gctctgcggg gctttgtgct ggcgccgctc ttcgtctatc tgttcatcgg cacctctttc | 1500 |
| ctgctggctg gtttcgtgtc gctcttccgc atccgcacca tcatgaagca tgacggcacc | 1560 |
| aagacagaga aactggaaaa gctcatggtg cgcatcggag tcttcagtgt gctctacacc | 1620 |
| gtgccggcca ccatcgtcat cgcctgctac ttctatgagc aggcctttcg ggaccagtgg | 1680 |
| gagcgcagct gggtggccca gagctgcaag agttatgcca tcccttgccc tcacctccaa | 1740 |
| ggaggtggag gcgtcccacc acacccaccc atgagcccg actttacagt cttcatgatc | 1800 |
| aagtatctca tgacgctaat tgtgggcatc acatcaggct tctggatctg tccggcaag | 1860 |
| acactgaatt cctggaggaa gttctacacg aggcttacca acagcaaaca gggggagact | 1920 |
| accgtc | 1926 |

<210> SEQ ID NO 8
<211> LENGTH: 2829
<212> TYPE: DNA
<213> ORGANISM: Homo sapiens

<400> SEQUENCE: 8

| | |
|---|---|
| atgcgaccct ccgggacggc cggggcagcg ctcctggcgc tgctggctgc gctctgcccg | 60 |
| gcgagtcggg ctctggagga aagaaaggt aattatgtgg tgacagatca cggctcgtgc | 120 |
| gtccgagcct gtggggccga cagctatgag atggaggaag acggcgtccg caagtgtaag | 180 |
| aagtgcgaag ggccttgccg caaagtgtgt aacggaatag gtattggtga atttaaagac | 240 |
| tcactctcca taaatgctac gaatattaaa cacttcaaaa actgcacctc catcagtggc | 300 |
| gatctccaca tcctgccggt ggcatttagg ggtgactcct tcacacatac tcctcctctg | 360 |
| gatccacagg aactggatat tctgaaaacc gtaaaggaaa tcacagggtt tttgctgatt | 420 |
| caggcttggc ctgaaaacag gacggacctc catgcctttg agaacctaga aatcatacgc | 480 |
| ggcaggacca gcaacatgg tcagttttct cttgcagtcg tcagcctgaa cataacatcc | 540 |
| ttgggattac gctccctcaa ggagataagt gatggagatg tgataatttc aggaaacaaa | 600 |
| aatttgtgct atgcaaatac aataaactgg aaaaaactgt ttgggacctc cggtcagaaa | 660 |
| accaaaatta taagcaacag aggtgaaaac agctgcaagg ccacaggcca ggtctgccat | 720 |
| gccttgtgct cccccgaggg ctgctggggc ccggagccca ggactgcgt ctcttgccgg | 780 |
| aatgtcagcc gaggcaggga atgcgtggac aagtgcaacc ttctggaggg tgagccaagg | 840 |
| gagtttgtgg agaactctga gtgcatacag tgccacccag agtgcctgcc tcaggccatg | 900 |
| aacatcaccct gcacaggacg gggaccagac aactgtatcc agtgtgccca ctacattgac | 960 |
| ggcccccact gcgtcaagac ctgcccggca ggagtcatgg agaaaacaa caccctggtc | 1020 |
| tggaagtacg cagacgccgg ccatgtgtgc caccttgtgcc atccaaactg cacctacgga | 1080 |
| tgcactgggc caggtcttga aggctgtcca acgaatgggc taagatcccg tccatcgcc | 1140 |
| actgggatgg tggggcccct cctcttgctg ctggtggtgg ccctgggat cggcctcttc | 1200 |
| atgcgaaggc gccacatcgt tcggaagcgc acgctgcgga ggctgctgca ggagagggag | 1260 |
| cttgtggagc tcttacacc cagtggagaa gctcccaacc aagctctctt gaggatcttg | 1320 |
| aaggaaactg aattcaaaaa gatcaaagtg ctgggctccg gtgcgttcgg cacggtgtat | 1380 |
| aagggactct ggatcccaga aggtgagaaa gttaaaattc ccgtcgctat caaggaatta | 1440 |
| agagaagcaa catctccgaa agccaacaag gaaatcctcg atgaagccta cgtgatggcc | 1500 |
| agcgtggaca accccccacgt gtgccgcctg ctgggcatct gcctcacctc caccgtgcaa | 1560 |

-continued

```
ctcatcacgc agctcatgcc cttcggctgc ctcctggact atgtccggga acacaaagac    1620
aatattggct cccagtacct gctcaactgg tgtgtgcaga tcgcaaaggg catgaactac    1680
ttggaggacc gtcgcttggt gcaccgcgac ctggcagcca ggaacgtact ggtgaaaaca    1740
ccgcagcatg tcaagatcac agattttggg ctggccaaac tgctgggtgc ggaagagaaa    1800
gaataccatg cagaaggagg caaagtgcct atcaagtgga tggcattgga atcaatttta    1860
cacagaatct atacccacca gagtgatgtc tggagctacg gggtgaccgt ttgggagttg    1920
atgacctttg gatccaagcc atatgacgga atccctgcca gcgagatctc ctccatcctg    1980
gagaaaggag aacgcctccc tcagccaccc atatgtacca tcgatgtcta catgatcatg    2040
gtcaagtgct ggatgataga cgcagatagt cgcccaaagt tccgtgagtt gatcatcgaa    2100
ttctccaaaa tggcccgaga cccccagcgc taccttgtca ttcagggggga tgaaagaatg    2160 catttgccaa gtcctacaga ctccaacttc taccgtgccc tgatggatga agaagacatg    2220
gacgacgtgg tggatgccga cgagtacctc atcccacagc agggcttctt cagcagcccc    2280
tccacgtcac ggactcccct cctgagctct ctgagtgcaa ccagcaacaa ttccaccgtg    2340
gcttgcattg atagaaatgg gctgcaaagc tgtcccatca aggaagacag cttcttgcag    2400
cgatacagct cagaccccac aggcgccttg actgaggaca gcatagacga caccttcctc    2460
ccagtgcctg aatacataaa ccagtccgtt cccaaaaggc ccgctggctc tgtgcagaat    2520
cctgtctatc acaatcagcc tctgaacccc gcgcccagca gagacccaca ctaccaggac    2580
ccccacagca ctgcagtggg caaccccgag tatctcaaca ctgtccagcc cacctgtgtc    2640
aacagcacat tcgacagccc tgcccactgg gcccagaaag gcagccacca aattagcctg    2700
gacaaccctg actaccagca ggacttcttt cccaaggaag ccaagccaaa tggcatcttt    2760
aagggctcca cagctgaaaa tgcagaatac ctaagggtcg cgccacaaag cagtgaattt    2820
attggagca                                                            2829
```

METHOD OF ANALYZING BINDING ASPECT OF MEMBRANE PROTEIN IN A LIVING CELL

RELATED APPLICATIONS

This application is a 35 U.S.C. §371 national phase application of PCT/KR2014/004426 (WO2014/185752), filed on May 16, 2014 entitled "Method for Analyzing Pattern of Live Intercellular Membrane Protein Binding", which application claims priority to and the benefit of Korean Patent Application No. 10-2013-0056008, filed May 16, 2013; and Korean Patent Application No. 10-2014-0059027, filed May 16, 2014; this application is also a continuation of PCT Application No. PCT/KR2013/011002, filed May 16, 2013, the disclosures of each are incorporated herein by reference in their entirety.

SEQUENCE STATEMENT

Incorporated by reference herein in its entirety is the Sequence Listing entitled "G15U11C0383P_ST25," created Nov. 16, 2015, size of 15 kilobyte.

TECHNICAL FIELD

The present invention relates to a method of analyzing a binding aspect between a membrane protein and a candidate material in a living cell.

BACKGROUND ART

A cell membrane is an essential factor for maintaining a cell, and membrane proteins localized in the cell membrane play an important role in intracellular and extracellular communication through dynamic interaction with ligands. Substantially, about a half of cellular proteins are known to be able to interact with ligands in the cell membrane, but huge parts still remain unknown. To figure out such interactions, a variety of techniques and attempts have been conducted over the years, and researchers are still making efforts.

Since an extracellular environment has a relatively very small viscosity, compared to an inside of the cell membrane, the influence of an extracellular domain of the membrane protein which directly binds to ligands on the diffusivity of target proteins has been ignored, and many researches relating to the diffusion theory of membrane proteins, which is the Saffman-Delbruck model, focus on a transmembrane domain to determine such diffusivity of the membrane proteins and describe its importance on membrane protein diffusion. Therefore, it has been considered that it is fundamentally difficult to measure the binding of ligands to the extracellular domain of the target membrane protein based on diffusion of membrane protein. However, since a system used in the conventional research could measure the interaction between target membrane protein and ligand only in an artificial and controlled environment using purified membrane proteins in vitro or inserting the target membrane protein into an artificially formed lipid membrane, such previous researches cannot reflect the complicated structure of an actual cell membrane, and thus the analysis of the interactions involving extracellular domain of membrane proteins with ligands has been limited.

DISCLOSURE

Technical Problem

The present invention is directed to providing a method of sensitively analyzing a binding aspect between a target membrane protein and a candidate material that can specifically bind thereto in a living single cell.

The present invention is also directed to providing a method of screening a drug for a target membrane protein.

However, the technical objectives to be accomplished by the present invention are not limited to the above-described problems, and other objectives not described herein will be fully understood by those of ordinary skill in the art from the following descriptions.

Technical Solution

In one aspect, one exemplary embodiment of the present invention provides a method of analyzing a binding aspect between a candidate material and a target membrane protein, the method including: calculating a diffusion coefficient of target membrane protein before and after treatment of the candidate material in a living cell expressing the target membrane protein; and analyzing a change in diffusion coefficient of at least one target membrane protein obtained thereby.

Also, in another aspect, another exemplary embodiment of the present invention provides a method of screening a drug for a target membrane protein, the method including: analyzing a binding aspect between a candidate material and a target membrane protein; and determining a drug specifically acting on the target membrane protein among the candidate materials using the binding aspect.

Hereinafter, the present invention will be described in detail.

The present invention provides a method of analyzing a binding aspect between a candidate material and a target membrane protein, the method including: measuring a diffusion coefficient of the target membrane protein before and after the candidate material is treated in a living cell expressing the target membrane protein; and analyzing a change in diffusion coefficient of at least one target membrane protein obtained thereby.

A variety of dynamic interaction between membrane proteins and ligands is one of the cellular responses to various environmental changes. A complex of the membrane protein bound with various ligands serves in various roles. However, since the identification of such a membrane protein complex is technically limited, much of the complex is still unknown. To overcome such a limitation, the inventors completed a single molecule diffusional motion shift assay (smDIMSA) in which single particle tracking (SPT) combined with super-resolution microscopy is utilized, and this method can be applied as a method of analyzing a binding aspect between a candidate material and a target membrane protein. Because smDIMSA sensitively detects a change in diffusion coefficient in a living cell, it can be used to study a biological reaction in an actual environment in which cells are alive and properly functioning, not in an artificially-created environment.

The analysis method of the present invention has the following characteristics (1) to (3) by detecting the fluorescence of a fluorescent protein directly conjugated to target membrane protein or fluorescent dyes linked to the probe which specifically binds to the target membrane protein:

(1) Non-labeling of ligands and direct binding measurement;

(2) Ligand-receptor specificity; and (3) Size sensitivity.

With reference to (1), when conventional flow cytometry, FRET or a different fluorescence-based assay is used, a candidate material, as well as a membrane protein, needs to be simultaneously labeled with a fluorescent material. Therefore, when using various candidate materials, it requires separate labeling to each candidate materials. However, since the candidate material does not need to be labeled in the method of the present invention, it has an advantage in that the binding can be determined only by the change in diffusion coefficient without additional fluorescence.

With reference to (2), to use the method of the present invention, a fluorescent protein linked directly to target membrane protein or a fluorescent dye conjugated probe which specifically binds to target membrane protein are utilized to detect target membrane protein, and therefore the method of the present invention has an advantage in that other neighboring membrane proteins do not affect the measurement results during observation.

With reference to (3), a change in diffusion coefficient which is related with the size is observed, and therefore the method of the present invention has an advantage in which the size of an unknown material can be estimated by the change in diffusion coefficient.

Because of the characteristics (1) to (3), the method of the present invention may be applied to a variety of fields of membrane protein research including (a) a dissociation constant, (b) a mutant study, (c) complex formation, and (d) signal transduction.

With reference to (a), the dissociation constant is an important parameter capable of estimating a binding strength between a membrane protein and a ligand in the field of biochemistry or pharmacology. The actual dissociation constant is generally measured from a purified protein of interest through surface plasmon resonance (SPR) or a filter binding assay. However, since the membrane protein is difficult to purify because of its characteristics, the measurement of dissociation constant of membrane protein has also been experiencing difficulties. If there are two different groups at the same time, a ratio between two groups may be estimated by the above-described method. Since, according to the method, a ligand-binding group and an unbound group have different sizes, the difference in diffusion coefficients between the groups can be distinguished, and thus the dissociation constant can be quantitatively measured using the above ratio at a single cell level.

With reference to (b), a mutant protein is used as an important marker for diagnosing a disease. If the binding between a mutant protein and a ligand in a cell is understood, a mutant signal can be distinguished from signals of mixed cells, and this can be of great help in disease research. Only specific binding originating from mutant proteins with respect to the mutant proteins that are mixed with normal proteins may be observed by the method of the present invention, and therefrom mutant protein-specific characteristics may be analyzed.

With reference to (c), proteins generally form an enormous molecular complex and play specific roles. However, since a membrane protein is difficult to purify and isolate, it is difficult to carry out research on the formation of a molecular complex. However, according to the method of the present invention, since the molecular size becomes larger during the formation of such a complex and directly affects to a diffusion coefficient, a process of forming the complex can be figured out.

The following examples show that binding between a target membrane protein and a candidate material can be measured by the analysis of a change in diffusion coefficient, for example, an EGFR antibody and its binding to EGFR is identified by a change in diffusion coefficient (refer to FIGS. 5 and 13), and binding between GPCR and a G protein can be detected by a chemical inhibitor treatment (refer to FIG. 7). Also, FIG. 19 shows that a molecular weight can be estimated only by measuring a diffusion coefficient through a correlation between the change in diffusion coefficient and the molecular weight of the candidate material. Also, FIG. 21 shows that a ratio of cetuximab-bound EGFR can be analyzed by the result of measuring the change in diffusion coefficient by treating gradually increasing concentration of cetuximab (candidate material). Accordingly, the plot shown in FIG. 22 may be obtained, and a dissociation constant Kd and binding cooperativity may also be obtained therefrom. Examples of the process of forming a complex can be found in FIGS. 27 and 28. It can be confirmed that the formation of an antibody complex is detected using a second antibody against the primary antibody directly binding to a target membrane protein, and a third antibody against the second antibody.

Meanwhile, in the present invention, the membrane protein refers to a protein binding to a membrane of cells or cell organelles, and the target membrane protein refers to a desired membrane protein to be observed among numerous membrane proteins present in a membrane. The membrane protein includes an integral membrane protein, a peripheral membrane protein, a transmembrane protein, a membrane glycoprotein, and a lipid anchored membrane protein.

For example, the membrane protein may include a receptor tyrosine kinase (RTK), a G protein coupled receptor (GPCR), an ion-channel, a pattern recognition receptor (PRR), etc. as an integral membrane protein.

For example, the RTK includes RTK class I, RTK class II, RTK class III, RTK class IV, RTK class V, RTK class VI, RTK class VII, RTK class VIII, RTK class IX, RTK class X, RTK class XI, RTK class XII, RTK class XIII, RTK class XIV, RTK class XV, RTK class XVI, RTK class XVII, etc. The RTK class I is an EGF receptor family or ErbB family, and includes ErbB-1 (EGFR), ErbB-2, ErbB-3, and ErbB-4, etc., the RTK class II is an insulin receptor family and includes insulin receptor-A, insulin receptor-B, etc., the RTK class III is a PDGF receptor family and includes PDGF-A, PDGF-B, PDGF-C, and PDGF-D, etc., the RTK class IV is an FGF receptor family and includes FGFR1, FGFR2, FGFR3, FGFR4, FGFR6, etc., the RTK class V is a VEGF receptors family and includes VEGFR-1, VEGFR-2, VEGFR-3, etc., the RTK class VI is a HGF receptor family and includes HGFR, etc., the RTK class VII is a Trk receptor family and includes TrkA, TrkB, TrkC, etc., the RTK class VIII is an EPH receptor family and includes EPHA1, EPHA2, EPHA3, EPHA4, EPHA5, EPHA6, EPHA7, EPHA8, EPHA9, EPHA10, EPHB1, EPHB2, EPHB3, EPHB4, EPHB5, EPHB6, etc., the RTK class IX is an AXL receptor family and includes AXL, etc., the RTK class X is an LTK receptor family and includes LTK, etc., the RTK class XI is a TIE receptor family and includes TIE1, TIE2, etc., the RTK class XII is an ROR receptor family and includes ROR1, ROR2, etc., the RTK class XIII is a DDR receptor family and includes DDR1, etc., the RTK class XIV is an RET receptor family and includes RET, etc., the RTK class XV is a KLG receptor family and includes PTK7, etc., the RTK class XVI is an RYK receptor family and includes RYK, etc., and the RTK class XVII is an MuSK receptor family and includes MuSK, etc.

The GPCR includes Class A (Rhodopsin-like), Class B (Secretin receptor family), Class C (Metabotropic glutamate/pheromone), Class D (Fungal mating pheromone receptors), Class E (Cyclic AMP receptors), Class F (Frizzled/Smoothened), etc. Class A has Subfamilies A1 to A19, wherein Subfamily A1 includes chemokine (C-C motif) receptor 1, chemokine (C-C motif) receptor 2, chemokine (C-C motif) receptor 3, chemokine (C-C motif) receptor 4, chemokine (C-C motif) receptor 5, chemokine (C-C motif) receptor 8, chemokine (C-C motif) receptor-like 2, chemokine (C motif) receptor 1, chemokine (C-X3-C motif) receptor 1, and GPR137B, etc.; Subfamily A2 includes chemokine (C-C motif) receptor-like 1, chemokine (C-C motif) receptor 6, chemokine (C-C motif) receptor 7, chemokine (C-C motif) receptor 9, chemokine (C-C motif) receptor 10, chemokine (C-X-C motif) receptor 3, chemokine (C-X-C motif) receptor 4, chemokine (C-X-C motif) receptor 5, chemokine (C-X-C motif) receptor 6, chemokine (C-X-C motif) receptor 7, IL8R-α, IL8R-β, adrenomedullin receptor, Duffy blood group, chemokine receptor, G protein-coupled receptor 30, etc.; Subfamily A3 includes angiotensin II receptor, apelin receptor, bradykinin receptor B1, bradykinin receptor B2, GPR15, GPR25, etc.; Subfamily A4 includes delta opioid receptor, kappa opioid receptor, mu opioid receptor, nociceptin receptor, somatostatin receptor 1, somatostatin receptor 2, somatostatin receptor 3, somatostatin receptor 4, somatostatin receptor 5, GPCR neuropeptides B/W receptor 1, neuropeptides B/W receptor 2, GPR1 orphan receptor, etc.; Subfamily A5 includes galanin receptor 1, galanin receptor 2, galanin receptor 3, cysteinyl leukotriene receptor 1, cysteinyl leukotriene receptor 2, leukotriene B4 receptor, leukotriene B4 receptor 2, relaxin/insulin-like family peptide receptor 1, relaxin/insulin-like family peptide receptor 2, relaxin/insulin-like family peptide receptor 3, relaxin/insulin-like family peptide receptor 4, KiSS1-derived peptide receptor (GPR54), melanin-concentrating hormone receptor 1, urotensin-II receptor, etc.; Subfamily A6 includes cholecystokinin A receptor, cholecystokinin B receptor, neuropeptide FF receptor 1, neuropeptide FF receptor 2, hypocretin (orexin) receptor 1, hypocretin (orexin) receptor 2, arginine vasopressin receptor 1A, arginine vasopressin receptor 1B, arginine vasopressin receptor 2, gonadotrophin releasing hormone receptor, pyroglutamylated RFamide peptide receptor, GPR22, GPR176, etc.; Subfamily A7 includes bombesin-like receptor 3, neuromedin B receptor, gastrin-releasing peptide receptor, endothelin receptor type A, endothelin receptor type B, GPR37, neuromedin U receptor 1, neuromedin U receptor 2, neurotensin receptor 1, neurotensin receptor 2, thyrotropin-releasing hormone receptor, growth hormone secretagogue receptor, GPR39, motilin receptor, etc.; Subfamily A8 includes C3a receptor, C5a receptor, chemokine-like receptor 1, formyl peptide receptor 1, formyl peptide receptor-like 1, formyl peptide receptor-like 2, MAS1, MAS1L, GPR1, GPR32, GPR44, GPR77, etc.; Subfamily A9 includes melatonin receptor 1A, melatonin receptor 1B, tachykinin receptor 1, tachykinin receptor 2, tachykinin receptor 3, neuropeptide Y receptor Y1, neuropeptide Y receptor Y2, pancreatic polypeptide receptor 1, neuropeptide Y receptor Y5, prolactin-releasing peptide receptor, prokineticin receptor 1, prokineticin receptor 2, GPR19, GPR50, GPR75, GPR83, etc.; Subfamily A10 includes FSH-receptor, luteinizing hormone/choriogonadotropin receptor, thyrotropin receptor, leucine-rich repeat-containing G protein-coupled receptor 4, leucine-rich repeat-containing G protein-coupled receptor 5, leucine-rich repeat-containing G protein-coupled receptor 6, etc.; Subfamily A11 includes free fatty acid receptor 1, free fatty acid receptor 2, free fatty acid receptor 3, GPR42, purinergic receptor P2Y1, purinergic receptor P2Y2, purinergic receptor P2Y4, purinergic receptor P2Y6, purinergic receptor P2Y8, purinergic receptor P2Y11, hydroxycarboxylic acid receptor 1, hydroxycarboxylic acid receptor 2, niacin receptor 1, hydroxycarboxylic acid receptor 3, niacin receptor 2, GPR31, GPR82, oxoglutarate (alpha-ketoglutarate) receptor 1, succinate receptor 1, etc.; Subfamily A12 includes purinergic receptor P2Y12, purinergic receptor P2Y13, purinergic receptor P2Y14, GPR34, GPR87, GPR171, platelet-activating factor receptor, etc.; Subfamily A13 includes cannabinoid receptor 1 (brain), cannabinoid receptor 2 (macrophage), lysophosphatidic acid receptor 1, lysophosphatidic acid receptor 2, lysophosphatidic acid receptor 3, sphingosine 1-phosphate receptor 1, sphingosine 1-phosphate receptor 2, sphingosine 1-phosphate receptor 3, sphingosine 1-phosphate receptor 4, sphingosine 1-phosphate receptor 5, melanocortin 1 receptor, melanocortin 3 receptor, melanocortin 4 receptor, melanocortin 5 receptor, ACTH receptor, GPR3, GPR6, GPR12, etc.; Subfamily A14 includes prostaglandin D2 receptor, prostaglandin E1 receptor, prostaglandin E2 receptor, prostaglandin E3 receptor, prostaglandin E4 receptor, prostaglandin F receptor, prostaglandin I2 (prostacyclin) receptor, thromboxane A2 receptor, etc.; Subfamily A15 includes lysophosphatidic acid receptor 4, lysophosphatidic acid receptor 5, lysophosphatidic acid receptor 6, purinergic receptor P2Y10, coagulation factor II (thrombin) receptor-like 1, coagulation factor II (thrombin) receptor-like 2, coagulation factor II (thrombin) receptor-like 3, lymphocyte-specific G protein-coupled receptor, GPR4, GPR65, GPR68, GPR132, GPR17, GPR18, GPR20, GPR35, GPR55, coagulation factor II receptor, etc.; Subfamily A16 includes rhodopsin, opsin 1 (cone pigments), opsin 3, panopsin, opsin 4, melanopsin, opsin 5, retinal G protein coupled receptor, and retinal pigment epithelium-derived rhodopsin homologs, etc.; Subfamily A17 includes 5-HT2A, 5-HT2B, 5-HT2C, 5-HT6, alpha1A, alpha1B, alpha1D, alpha2A, alpha2B, alpha2C, beta1, beta2, beta3, D1, D2, D3, D4, D5, TAAR1, TAAR2, TAAR3, TAAR5, TAAR6, TAAR8, TAAR9, histamine H2 receptor, etc.; Subfamily A18 includes histamine H1 receptor, histamine H3 receptor, histamine H4 receptor, adenosine receptor (A1, A2a, A2b, A3), muscarinic acetylcholine receptor (M1, M2, M3, M4, M5), GPR21, GPR27, GPR45, GPR52, GPR61, GPR62, GPR63, GPR78, GPR84, GPR85, GPR88, GPR101, GPR161, GPR173, etc.; and Subfamily A19 includes 5-Hydroxytryptamine (5-HT) receptors (5-HT1A, 5-HT1B, 5-HT1D, 5-HT1E, 5-HT1F, 5-HT4, 5-HT5A, 5-HT7), and additionally, unclassified olfactory receptors vomeronasal receptors (VN1R1, VN1R2, VN1R3, VN1R4, VN1R5), etc. Class B has Subfamilies B1 to B3, wherein Subfamily B1 includes pituitary adenylate cyclase-activating polypeptide type 1 receptor (PACAPR), calcitonin receptor (CALCR), corticotropin-releasing hormone receptor (CRHR1, CRHR2), glucose-dependent insulinotropic polypeptide receptor/gastric inhibitory polypeptide receptor (GIPR), glucagon receptor-related (GLP1R, GLP2R), growth hormone releasing hormone receptor (GHRHR), parathyroid hormone receptor (PTHR1, PTHR2), secretin receptor (SCTR), vasoactive intestinal peptide receptor (VIPR1, VIPR2), etc.; Subfamily B2 includes brain-specific angiogenesis inhibitor (BAI1, BAI2, BAI3), CD97 antigen (CD7), EMR hormone receptor (CELSR1, CELSR2, CELSR3, EMR1, EMR2, EMR3, EMR4), GPR56 orphan receptor IPR003910 (GPR56, GPR64, GPR97, GPR110, GPR111, GPR112, GPR113, GPR114, GPR115, GPR123, GPR125, GPR126, GPR128, GPR133, GPR144, GPR157), Latrophilin receptor IPR003924 (ELTD1, LPHN1, LPHN2, LPHN3), etc.; subfamily B3 includes diuretic hormone receptor; and unclassified subfamilies includes Ig-hepta receptor (GPR116). Class C includes Group I (mGluR1, mGluR5), Group II (mGluR2, mGluR3), and Group III (mGluR4, mGluR6, mGluR7, mGluR8) as a metabotropic glutamate/pheromone, etc., Class D includes STE2, STE3, etc. as a fungal mating pheromone receptor, Class E includes cyclic AMP receptors, and Class F includes Frizzled-1, Frizzled-2, Frizzled-3, Frizzled-4, Frizzled-5, Frizzled-6, Frizzled-7, Frizzled-8, Frizzled-9, Frizzled-10, etc. as Frizzled/Smoothened.

The ion-channels include voltage-gated ion channels (voltage-gated sodium channel, voltage-gated calcium channel, voltage-gated potassium channel, transient receptor potential channel, cyclic nucleotide-gated channel, and voltage-gated proton channel), ligand-gated ion channels, vertebrate anionic cys-loop receptors (GABAA and GlyR), vertebrate cationic cys-loop receptors (serotonin, nicotinic acetylcholine, and zinc-activated ion channel), ionotropic glutamate receptors (AMPA, kainate, NMDA, and orphan), and ATP-gated channels (P2X), etc.

The PRRs include receptor kinases, toll-like receptors (TLR) (TLRs in *drosophila* immunity, TLR3, TLR11), and C-type lectin receptors (CLR) including Group I CLRs that is the mannose receptors, and Group II CLRs, which is the asialoglycoprotein receptor family that contains the classic asialoglycoprotein receptor macrophage galactose-type lectin (MGL), DC-SIGN (CLEC4L), Langerin (CLEC4K), Myeloid DAP12-associating lectin (MDL)-1 (CLEC5A), DC-associated C-type lectin 1 (Dectin1) subfamily (dectin 1/CLEC7A, DNGR1/CLEC9A, Myeloid C-type lectin-like receptor (MICL) (CLEC12A), CLEC2, CLEC12B), and DC immunoreceptor (DCIR) subfamily (DCIR/CLEC4A, Dectin 2/CLEC6A, Blood DC antigen 2 (BDCA2) (CLEC4C), Mincle i.e. macrophage-inducible C-type lectin (CLEC4E)), etc.

Also, in the present invention, the candidate material is a material binding to a target membrane protein to activate the target membrane protein, for example, a compound, a nucleic acid, a saccharide, a carbohydrate, a lipid, a peptide, or a protein. The protein may be, for example, an antibody, and here, the antibody includes all or a part thereof, for example, a Fab domain or a domain from which only a hinge part is selectively removed (half-immunoglobulin fragment). In one exemplary embodiment, the candidate material may be a nucleic acid, and here, the nucleic acid includes all of oligonucleotides including 2 to 200 bases or cDNAs thereof. Cells may be treated with the candidate material at an amount suitable for analyzing a binding aspect of a target membrane protein, and the treatment may be carried out by a method known in the art. For example, 0.01 to 100 μg/ml of the candidate material may be directly applied to a medium of the cells.

In one exemplary embodiment, a diffusion coefficient of a target membrane protein may be obtained by detecting a motion of the membrane protein in a cell membrane through single particle tracking (SPT). The SPT is technology of observing the motion of single particles in a certain medium, presenting coordinates of the motion over time as a trajectory, and therefrom analyzing a mode of the motion and non-uniformity (Saxton, M. J., Jacobson, K. Single-particle tracking: Applications to membrane dynamics Annual Review of Biophysics and Biomolecular Structure 1997; 26 (373-399)).

The motion of the membrane proteins in the cell membrane may be detected by a method known in the art. For example, fluorescence may be detected by total internal reflection fluorescence (TIRF). A TIRF microscope can observe only fluorescence in a specific range of 200 nm or less to the exclusion of interference of other light using total internal reflection of light and therefore is suitable for research on a cell membrane and the events happening around the cell membrane. By using such a TIRF microscope, images are obtained about the positions of the target membrane protein over a series of time points, and the result is expressed as coordinates, thereby obtaining a diffusion coefficient.

The diffusion coefficient according to the present invention may be obtained using the following Equations 1 and 2. For example, the fluorescence of a fluorescent protein linked to the target membrane protein is detected, thereby obtaining several sequential images of positions of the target membrane protein over time, that is, coordinates for a predetermined period of time, and the motion of such coordinates may be expressed as one trajectory of the target membrane protein. Afterward, a diffusion coefficient with respect to one trajectory may be obtained by substituting the measured coordinates of the trajectory over time to the following Equations 1 and 2. To determine the position of one target membrane protein particle by the above-described calculation, an exposure time for detecting fluorescence (a time required to image the membrane-protein particle at one position in the coordinates) may be suitably changed depending on analysis conditions, and may be, for example, about 30 to 70 ms, preferably, 50 ms. Also, the number of pairs of coordinates necessary to make one trajectory of one target membrane protein particle may be, but is not limited to, 5 or more.

$$MSD(\Delta) = \frac{1}{N-\Delta}\sum_{n=1}^{N-\Delta}((x_{n+\Delta} - x_n)^2 + (y_{n+\Delta} - y_n)^2) \quad \text{[Equation 1]}$$

$\Delta$ is the step size between coordinates of the target membrane protein particle, wherein $\Delta$ is a natural number, MSD($\Delta$) is the mean square displacement of a target membrane protein particle with respect to the step size between coordinates of the target membrane protein particle, N is the total number of pairs of coordinates of the target membrane protein particle to form one trajectory, $(x_n, y_n)$ are the coordinates of the target membrane protein particle at an n-numbered position in one trajectory, $(x_1, y_1)$ are the coordinates of the target membrane protein particle at the start point in one trajectory, $(x_N, y_N)$ are the coordinates of the target membrane protein particle at the end point in one trajectory, and $(x_{n+\Delta}, y_{n+\Delta})$ are the coordinates of the target membrane protein particle at an n+$\Delta$-numbered position in one trajectory, however, n+$\Delta$ is the same as or smaller than N.

$$MSD(\Delta) = 4D\Delta \quad \text{[Equation 2]}$$

D is the diffusion coefficient, and $\Delta$ is the step size between coordinates of the target membrane protein particle.

According to such a calculation, MSD is referred to as a function of the step size between the coordinates of the target membrane protein particle. Assuming that the corresponding trajectory is subject to the Brownian motion, MSD is referred to as a linear function. Therefore, from the slope of the linear function (f(X)=aX) when MSD of the trajectory of each membrane protein is fitted to the linear function by Equation 2, a diffusion coefficient (a/4) of the trajectory may be obtained. Since MSD represents a mean value, more accurate diffusion coefficient may be obtained as there are more coordinates of the target membrane protein particle forming the corresponding trajectory (that is, as the tracked trajectory increases in length or a coordinate density is increased). Therefore, the calculation of the diffusion coefficient needs a trajectory with a predetermined length or more, and the fitting of the linear function uses two or more frames of the step size between the coordinates of the target membrane protein particle (because the fitting of the linear function is made possible with two points), thereby increasing the accuracy in the measurement of the diffusion coefficient. Such diffusion coefficients are averaged with respect to the total trajectory, a mean diffusion coefficient of the membrane protein in each cell may be calculated.

Also, a change in diffusion coefficient may be obtained by the following Equation 3:

$$\text{Change in diffusion coefficient (\%)} = 100 * |1 - (D_{c2}/D_{c1})| \quad \text{[Equation 3]}$$

In this formula, $D_{c1}$ is the diffusion coefficient of the target membrane protein at a concentration c1 of the candidate material in a peripheral environment of the cell at a single cell level, and $D_{c2}$ is the diffusion coefficient of the target membrane protein at a concentration c2 of the candidate material in a peripheral environment of the cell at a single cell level.

Since single membrane proteins on a living cell membrane of the present invention have a very high heterogeneity even though they are the same type of membrane proteins, a single cell-level change in diffusion coefficient may be analyzed by obtaining diffusion coefficients by tracking more than one trajectory of target single membrane protein. As the number of the detected target membrane proteins is increased, the analysis accuracy may increase. The number of the detected target membrane proteins and time to obtain the trajectory of the target membrane protein may vary depending on a type and characteristics of the target membrane protein and a type of cells, and may be suitably adjusted depending on analysis conditions by those of ordinary skill in the art. To precisely measure the change in diffusion coefficient at a single cell level, 1,000 or more, for example, 5,000 or more, preferably, 10,000 or more, more preferably 12,000 or more, still more preferably, 15,000 or more, and most preferably 20,000 or more target membrane proteins may be tracked, but the present invention is not limited thereto. Afterward, each diffusion coefficient is obtained by the trajectory obtained from each target membrane protein, and these values are averaged, thereby obtaining a more accurate diffusion coefficient. For example, when the trajectory of the target membrane protein that is maintained in a steady state and has a length of 5 or more continuous images (in order to obtain MSD in which N is 5 or more in Equation 1) is tracked in one cell during measurement, diffusion coefficient values with respect to about 12,000 or more trajectories may be obtained within 2 minutes (detecting about 24,000 images), and the resultant values may be averaged to ensure an error of the diffusion coefficients within 2% at a single cell level.

When comparing before and after the treatment with the candidate material, the size of target membrane protein is increased due to binding of the candidate material, and the diffusion coefficient of the target membrane protein is reduced, thus the binding status of the target membrane protein with the candidate material, a ratio of the target membrane proteins binding to the candidate material among the total target membrane proteins, the molecular weight of the candidate material can be analyzed using the degree of a change in the diffusion coefficient. Therefore, when there is a change in diffusion coefficient, the candidate material may be determined as a ligand binding to the target membrane protein. For example, when the change in diffusion coefficient (%) obtained from Equation 3 is, for example, at least 2% to 5% at a significance level, the candidate material may be determined as the ligand binding to the target membrane protein.

The motion of the membrane protein in the cell membrane may be detected by labeling the membrane protein with an optical probe such as a fluorescent probe, and as described above, the detection does not require labeling the candidate material, or the binding between the membrane protein and the candidate material.

In one exemplary embodiment of the present invention, the detection of the motion of the membrane protein in the cell membrane may be carried out by detecting the fluorescence of the fluorescent protein in cells expressing a fusion protein of the target membrane protein and the fluorescent protein. The fluorescent protein serves as a label to observe the target membrane protein, and a type of the fluorescent protein is not particularly limited. For example, the fluorescent protein may include a green fluorescent protein (GFP) type, a blue fluorescent protein (BFP) type, a cyan type, a yellow fluorescent protein (YFP) type, a red fluorescent protein (RFP) type, an orange type, a far-red type, a near-IR, a photoactivatable protein, a photoconvertible protein, a photoswitchable protein, etc. Here, the photoactivatable protein refers to a protein that does not fluoresce in normal circumstances, but fluoresces in response to certain stimuli (e.g., laser radiation). Also, the photoconvertible protein and the photoswitchable protein are proteins that showed a specific color of fluorescence in normal circumstances, and turned a different color of fluorescence because of certain stimuli like the photoactivatable protein, but such conversion is irreversible in the photoconvertible protein and reversible in the photoswitchable protein.

The GFP type includes enhanced green fluorescent protein (EGFP), Emerald, Superfolder GFP, Azami green mWasabi, TagGFP, AcGFP, T-sapphire, mUKG, Clover, mNeonGreen, etc., the blue fluorescent protein (BFP) type includes enhanced blue fluorescent protein (EBFP), EBFP2, Azurite, mTagBFP, mKalama1, Sirius, etc., the cyan type includes enhanced cyan fluorescent protein (ECFP), monomeric ECFP (mECFP), Cerulean, mTurquoise, mTurquoise2, CyPet, TagCFP, mTFP1 (Teal), SCFP3A, monomeric Midoriishi Cyan, etc., the YFP type includes enhanced yellow fluorescent protein (EYFP), Topaz, Benus, mCitrine, YPet, TagYFP, PhiYFP, mBanana, SYFP2, etc., the RFP type includes mRuby, mRuby2, mApple, mStrawberry, mRFP1, mCherry, mRaspberry, dKeima-Tandem (monomeric version), HcRed-Tandem (monomeric version), mPlum, etc., the Far-red type includes mKate2 mNeptune, etc., the Near-IR includes TagRFP657 IFP1.4, etc., the photoactivatable protein includes PA-GFP, PAmCherry1, PaTagRFP, etc., the photoconvertible protein includes PS-CFP2, mEos2, mEos3.2, PSmOrange, etc., and the photoswitchable protein includes Dronpa, etc.

For example, the fluorescent protein may include at least one selected from the group consisting of enhanced green fluorescent protein (EGFP), Emerald, Superfolder GFP, Azami green mWasabi, TagGFP, AcGFP, T-sapphire, mUKG, Clover, mNeonGreen, enhanced blue fluorescent protein (EBFP), EBFP2, Azurite, mTagBFP, mKalama1, Sirius, enhanced cyan fluorescent protein (ECFP), monomeric ECFP (mECFP), Cerulean, mTurquoise, mTurquoise2, CyPet, TagCFP, mTFP1 (Teal), SCFP3A, monomeric Midoriishi Cyan, enhanced yellow fluorescent protein (EYFP), Topaz, Benus, mCitrine, YPet, TagYFP, PhiYFP, mBanana, SYFP2, mRuby, mRuby2, mApple, mStrawberry, mRFP1, mCherry, mRaspberry, dKeima-Tandem (monomeric version), HcRed-Tandem (monomeric version), mPlum, mKate2, mNeptune, mKate2, mNeptune, TagRFP657, IFP1.4, PA-GFP, PAmCherry1, PaTagRFP, PS-CFP2, mEos2, mEos3.2, PSmOrange and Dronpa.

The fusion protein refers to a covalent complex formed by genetic fusion or a chemical bond between the target membrane protein and the fluorescent protein. The "genetic fusion" refers to a linear connection made by a covalent bond through genetic expression of a DNA sequence encoding the fusion protein. The formation of the fusion protein may be performed by a known method, for example, genetic recombination technology.

The cell expressing the fusion protein may be prepared by transformation with an expression vector. A known expression vector developed to express the fusion protein may be suitably selected. For example, the expression vector may be a plasmid vector, a virus or a cosmid vector. Host cells expressing the fusion protein may be prepared by a chemical treatment method such as a calcium phosphate method or calcium chloride/rubidium chloride method described in the literature (Sambrook, J., et al., Molecular Cloning, A Laboratory Manual (Second edition), Cold Spring Harbor Laboratory, 1. 74, 1989), electroporation, electroinjection or PEG, or a transformation method such as a method using a gene gun or virus transfection. For example, the cell expressing the fusion protein may be prepared by transfecting a host cell with an expression vector containing the fusion protein of the target membrane protein and the fluorescent protein using lipofectamine, fugene or metafectin.

The cells expressing the fusion protein of the target membrane protein and the fluorescent protein may be animal, plant, yeast and bacterial cells. For example, the cells may be human embryonic kidney (HEK) cells, HEK 293 cells (ATCC CRL 1573), 3T3-L1 cells (ATCC CL 173), C6 cells (ATCC CCL 107), CHO (Chinese hamster ovary) cells (ATCC CCL61), CHOK1 cells (ATCC CCL 61), NIH/3T3 (NIH Swiss mouse embryo) cells (ATCC CRL 1658), BHK (baby hamster kidney) cells, COS1 cells (ATCC CRL 1650), COS7 cells (ATCC CRL 1651), HaCaT cells, HeLa cells (ATCC CCL 2), HeLa S3 cells (ATCC CCL 2.2), HepG2 cells (ATCC HB 8065), HL-60 cells (ATCC CCL 240), HUV-EC-C cells (ATCC CRL 1730), Jurkat cells (ATCC TIB 152), K-562 cells (ATCC CCL 243), L6 cells (ATCC CRL 1458), MCF7 cells (ATCC HTP 22), MDCK cells (ATCC CCL 34), NIH/3T3 cells (ATCC CRL 1658), RAW 264.7 cells (ATCC TIB 71), RBL-1 cells (ATCC CRL 1378), SH-SY5Y cells (ATCC CRL 2266), or U-937 cells (ATCC CRL 1593.2).

In still another exemplary embodiment of the present invention, the motion of the membrane protein in the cell membrane may be detected with a fluorescent material-conjugated probe specifically binding to the target membrane protein. A method of detecting the change in diffusion coefficient using the fusion protein of the membrane protein and the fluorescent protein requires preparing cells which express the fusion protein whose diffusion coefficient will be detected, and has a disadvantage in that a type of the cells capable of expressing the fusion protein depending on a type of the target membrane protein is limited. However, since the method using the fluorescent material-conjugated probe does not have such a limitation and employs any cells expressing the target membrane protein, it can be usefully applied.

Any type of probe to which a fluorescent material is conjugated and which can specifically bind to the target membrane protein can be used. However, the probe specifically binding to the target membrane protein that does not affect an activity of the target membrane protein may be selected. Although not limited thereto, in one exemplary embodiment, the probe may be an antibody, an aptamer, or a non-antibody protein scaffold. The antibody includes a Fab antibody, a single chain variable fragment, and a single-domain antibody as well as an antibody having a full sequence. A trajectory can be tracked through the binding with the target membrane protein after a fluorescent material is conjugated to the antibody having a full sequence, but since the degree of a change in diffusion coefficient is reduced in the binding with a different bindable partner due to the size of a full antibody, a marker that maintains specificity of the antibody and has a size as small as possible may be preferable. Also, as well as the antibody, the aptamer or the non-antibody protein scaffold, conjugated to a fluorescent probe, may be useful for the method. The non-antibody protein scaffold is made by finding and optimizing a scaffold specifically binding to the target protein among random protein scaffolds, not based on an antibody and is, for example, a material such as an affibody.

A fluorescent material binding to the probe is not particularly limited. In one exemplary embodiment, the fluorescent material may be an organic fluorescent dye, and the organic fluorescent dye that can be used in the present invention may be selected from Atto 488, Alexa Flour 488, Dy505, Rhodamine 123, Atto 520, Dy 530, ATTO 532, Alexa Fluor 532, Fluorescein, FITC, Cy2, Cy3B, Alexa Flour 568, TAMRA, Cy3, Cy3.5, SNAP-Cell TMR-Star, Atto 565, Atto 590, Alexa Fluor 647, Cy5, Atto 647, Atto 647N, Dyomics 654, Atto 655, TMP-ATTO 655, Atto 680, Cy5.5, Atto 680, Alexa Fluor 680, Atto 700, Alexa Fluor 700, DyLight 750, Cy7, Alexa Flour 750, Atto 740, Alexa Flour 790, and IRDye 800 CW. Other than this, any organic fluorescent dye corresponding to a photoswitchable fluorescent dye may be used.

Meanwhile, the method of the present invention may further include obtaining diffusion coefficients of the target membrane protein after treatment with the candidate material at several points of time, and analyzing a change in diffusion coefficient of at least one target membrane protein obtained thereby over time. For example, a dissociation constant between the target membrane protein and the candidate material may be analyzed by detecting the fluorescence of the target membrane protein moving in a flexible membrane state over time.

Also, the analysis method may further include analyzing the change in diffusion coefficient of the target membrane protein over time to determine membrane protein-specific endocytosis. The endocytosis of the target membrane protein may be determined from a tracked trajectory based on the diffusion coefficient. During the endocytosis, the trajectory of the membrane protein particle has a confined motion which shows the motion of particles in a limited space having a size of about 120 nm, which is the size of a clathrin-coated particle (CCP), which is one of the endocytotic organelles, at a certain position while they freely diffuse. Therefore, the pattern of changing the trajectory of the particle from the free diffusion into the confined motion may be considered as the endocytosis. Since the endocytosis may be used as an important factor for determining an effect of a target-specific drug, when membrane protein-specific endocytosis is found by the treatment of the candidate material to target membrane protein, it can be expected that the candidate material has an effect as a target-specific drug.

According to the analysis method, the process of forming the complex of the target membrane protein and the candidate material may be analyzed by analyzing the change in diffusion coefficient of the target membrane protein over time. For example, the process of forming a complex of the target membrane protein and various candidate materials may be analyzed over time by analyzing the change in diffusion coefficient of the fusion protein by repeatedly adding the same or different candidate materials.

A binding aspect in a single cell may be analyzed by the above method. When a conventional art such as a biochemical method, more specifically, immunoprecipitation is used, about ten million cells are needed, but the method of the present invention can be used at a single-cell level, and therefore, the binding aspect to the target membrane protein may be analyzed only with a very small amount of the candidate materials.

In another aspect, the present invention provides a method of screening a drug for a target membrane protein, the method including: analyzing a binding aspect between a candidate material and a target membrane protein by the above-described method; and determining a drug specifically acting on the target membrane protein among the candidate materials using the binding aspect. In the screening method, the membrane protein, the candidate material, a diffusion coefficient, and the detection of the motion of the membrane protein in a cell membrane is as described above.

The membrane protein is a main target in drug development, and 50% or more of all of the drugs developed now target the membrane protein (Overington, J. P., How many drug targets are there?, Nature reviews. Drug discovery. 5, 993-996, 2006). For example, isoprenaline, which is a therapeutic agent for heart block or bradycardia, is a drug targeting a b-adrenergic receptor, and insulin, which is a diabetes therapeutic agent, is known as a drug targeting an insulin receptor (Peter Imming. et al. Drugs, their targets and the nature and number of drug target. Nature reviews. Drug discovery, 2006). Also, various developed anticancer agents are targeting the membrane protein. For example, the ErbB family plays an important role in cancer, and the importance on the development of an anticancer agent targeting the ErbB family is already known (Eric K. Rowinsky. THE ERBB FAMILY: Targets for Therapeutic Development Against Cancer and Therapeutic Strategies Using Monoclonal Antibodies and Tyrosine Kinase Inhibitors. Annu Rev. Med. 55, 433-57, 2004). For example, cetuximab, which is a colon cancer therapeutic agent, is a drug targeting the ErbB family. Therefore, research on binding between the membrane protein and a ligand may be applied to develop a drug specifically acting on the target membrane protein, and particularly, may be used as a method of screening a drug against the target membrane protein. For example, after cells expressing the target membrane protein are treated with the candidate material, when a change in diffusion coefficient (%) is in more than an error range of, for example, 2 to 5% at least, by Equation 3, the candidate material may be determined as a drug specifically acting on the target membrane protein.

Advantageous Effects

A method of analyzing a binding aspect according to the present invention is a method of accurately, sensitively, rapidly and easily analyzing the binding aspect between the target membrane protein and a candidate material specifically binding thereto without labeling a ligand, and therefore, a positional and quantitative information about the binding between the membrane protein and the candidate material may be directly and precisely measured. Due to such an effect, the method may be applied in various applications such as the measurement of a dissociation constant, a mutant study, complex formation, and signal transduction. Furthermore, the method is also expected to explore various membrane proteins and candidate materials, which are still unknown.

DESCRIPTION OF DRAWINGS

FIG. 1 is a schematic diagram of a system that can only specifically observe a target protein among various membrane proteins present in a cell membrane by labeling the target membrane protein with a fluorescent protein, under the environment of which binding of a ligand makes diffusion of the target protein slow.

FIG. 2 is a diagram illustrating a process of tracking the motion of a target membrane protein of one cell attached to a round coverslip by TIRF and spatio-temporally averaging the tracking result to analyze the diffusion coefficient of the target membrane protein in a single cell.

FIG. 3 illustrates randomly selected trajectories of PMT-mEos3.2 and EGFR-mEos3.2 before and after treatment with cetuximab to the host cells expressing each protein respectively, in which PMT has almost no change in length of the trajectory before and after the treatment with cetuximab, but EGFR shows absolutely shorter length of the trajectory after the treatment with cetuximab.

FIG. 4 illustrates the means and standard deviations of diffusion coefficients of PMT and EGFR before and after the treatment with cetuximab for 10 cycles according to Example 1.5.

FIG. 5 illustrates the quantitatively summarized results of FIG. 3.

FIG. 6 illustrates that β2-AR statically is not bound with a Gi-protein and thus has no difference even by the treatment with Pertussis toxin (PTX), but as FZD1 is bound with a Gi-protein, when treated with PTX, ADP of the Gi-protein is ribosylated, thereby inhibiting the binding with FZD1.

FIG. 7 illustrates changes in diffusion coefficients of PMT, FZD1 and β2-AR before and after PMT, FZD1 and β2-AR are treated with PTX according to Example 2.4.

FIG. 8 illustrates absolute values of averaged diffusion coefficients of PMT, β2-AR, EGFR according to Example 2.4.

FIG. 9 illustrates changes of diffusion coefficients of EGFR measured in different environments according to Example 3, in which batch#1, batch#2 and batch #3 represent changes in diffusion coefficient of EGFR in COS7 cells prepared in three different batches, and batch#3-1 and batch#3-2 are in the same batch, but represent changes in diffusion coefficient of EGFR measured at different glasses.

FIG. 10 illustrates changes in diffusion coefficient of EGFR in HEK293, HELA and CHO-K1 cells according to Examples 4 to 6.

FIG. 11 is a diagram illustrating antibodies capable of binding to EGFR at different sites, for example, cetuximab, mAb 199.12, mAb 528 and mAb R-1.

FIG. 12 illustrates western blotting results according to Comparative Example 1, in which NT represents a non-treatment state, and EGF+/− represents treatment/non-treatment of EGF.

FIG. 13 illustrates changes in diffusion coefficients of PMT and EGFR according to Example 7.

FIG. 14 illustrates cetuximab specifically binding to EGFR, and trastuzumab specifically binding to ErbB2.

FIG. 15 illustrates flow cytometry results according to Comparative Example 2, in which, particularly, the x axis represents the intensity of a fluorescent signal, and the y axis represents a relative ratio of the cell population having a specific level of the intensity of a fluorescent signal.

FIG. 16 is a graph illustrating changes in diffusion coefficients before and after PMT and EGFR are treated with cetuximab, trastuzumab, and an anti-actin antibody according to Example 8.

FIG. 17 is diagrams illustrating that EGFR is bound with four different ligands having different molecular weights at the same binding position.

FIG. 18 illustrates changes in diffusion coefficient of EGFR before and after PMT and EGFR are treated with cetuximab, cetuximab Fab, cetuximab F(ab')2, and EGFR-specific binding aptamer according to Example 9.

FIG. 19 illustrates that the molecular weight of the ligand and the change in diffusion coefficient have a linear relationship according to Example 9.

FIG. 20 is a diagram illustrating that EGFR-bound cetuximab increases in number as the concentration of cetuximab is increased according to Example 10.1.

FIG. 21 illustrates reduction in diffusion coefficient of EGFR as the concentration of cetuximab is increased from 0.02 to 1.28 µg/ml in a single cell.

FIG. 22 is a graph of a dissociation constant and cooperativity obtained by calculating the ratio of EGFR-bound cetuximab by increasing the concentration of cetuximab.

FIG. 23 illustrates that EGFR wild-type (WT, wild-type) can be bound with both of cetuximab and an mAb R-1 antibody, but a mutant, EGFRvIII, is bound with only cetuximab, and not an mAb R-1 antibody.

FIG. 24 illustrates that PMT is not bound with two antibodies such as cetuximab and mAb R-1, and thus has no reduction in diffusion coefficient of PMT, but EGFRvIII is not bound with mAb R-1 but bound with cetuximab and thus shows different change in diffusion coefficient.

FIG. 25 is a graph of a dissociation constant and cooperativity obtained by calculating a ratio of EGFRvIII-bound cetuximab by the method described in Example 10.1.

FIG. 26 illustrates that cetuximab, a secondary antibody, and a tertiary antibody that bind to EGFR in turn.

FIG. 27 illustrates that the diffusion coefficient of EGFR is gradually reduced when EGFR is treated with the cetuximab, secondary antibody, and tertiary antibody in turn.

FIG. 28 illustrates the changes in diffusion coefficient of EGFR when the EGFR is sequentially treated with the cetuximab, tertiary antibody, and secondary antibody.

FIG. 29 illustrates a process of detecting endogenous EGFR by conjugating a photoswitchable fluorescent organic dye, Alexa Fluor 647, to a Fab fragment capable of specifically binding to the endogenous EGFR.

FIG. 30 illustrates that the binding of mAb 199.12 to the endogenous EGFR does not interfere with the binding of cetuximab.

FIG. 31 illustrates a specific binding aspect between the endogenous EGFR and cetuximab.

FIG. 32 is the quantitative results of the means and standard deviations of diffusion coefficients changed by treatment of an immunoglobulin antibody and cetuximab in five different cell lines.

FIG. 33 is images of mouse primary cells classified by marker expressions of cell types in lung cell tissues and autofluorescence levels.

FIG. 34 illustrates the changes in diffusion coefficient depending on a binding aspect of cetuximab to endogenous EGFRs present in four types of cells selected in FIG. 33, which are BASCs, endothelial cells, AT2 cells, and Clara cells.

BEST MODE

Hereinafter, the present invention will be described in further detail with reference to the following examples. However, the following examples are merely provided to illustrate the present invention, and the scope of the present invention is not limited to the following examples.

EXAMPLES

Example 1. Measurement of Target Membrane Protein: EGFR 1.1 Plasmid for Preparing EGFR-mEos3.2 Fusion Protein EGFR WT (Addgene plasmid #11011) used in the experiment was provided by Dr. Matthew Meyerson, and mEos3.2 fluorescent protein was provided by Dr. Tao xu. The given fluorescent protein was subcloned from pEGFP-N1/mEos3.2 to form pcDNA3.1/mEos3.2-his in order to facilitate binding with a membrane protein. To prepare a protein in which the membrane protein EGFR WT (SEQ ID NO: 1) is linked with the fluorescent protein mEos3.2 (SEQ ID NO: 2), pcDNA3.1/EGFR WT-mEos3.2-His was constructed using restriction enzymes such as XbaI (SEQ ID NO: 3, TCTAGA) and NotI (SEQ ID NO: 4, GCGGCCGC).

1.2 Plasmid for Preparing PMT-mEos3.2 Fusion Protein

A plasmid in which PMT is linked with a fluorescent protein was prepared to be used as a control group for Example 1.1. DNA (SEQ ID NO: 5) corresponding to PMT was inserted into the subcloned pcDNA3.1/mEos3.2-his using restriction enzymes such as XbaI (SEQ ID NO: 3) and NotI (SEQ ID NO: 4), thereby constructing pcDNA3.1/PMT-mEos3.2-His.

1.3 Preparation of Host Cells for Expressing Fusion Protein

COS7 cells provided by ATCC were grown in DMEM (Dulbecco's Modified Eagle Medium, Lonza) under conditions of 37° C., 5% $CO_2$, and 95% humidity, with 10% FBS (Gibco), and COS7 cells were transfected with each of the plasmids constructed in Examples 1.1 and 1.2 using Lipofectamine 2000 (Invitrogen) according to the manufacturer's instruction. To reduce the influence of protein overexpression, cells showing especially low expression level were sorted from the cells grown for 24 hours after transfection through flow cytometry. In detail, the transfected cells were washed with PBS to remove debris, detached from a bottom using a detaching buffer, and collected and strained with a cell strainer (40 µm, BD Bioscience). Afterward, the cells showing low expression level were specifically sorted using a MoFlo™ XDP cell sorter (Beckman Coulter).

The sorted cells were seeded on a 25-mm-diameter coverslip. Before use, the coverslip was prepared by procedures of sonication in acetone at 42° C. for 30 minutes to minimize autofluorescence of the coverslip, washing with distilled water three times, sonication again in 1% hydrofluoric acid at 42° C. for 10 minutes, washing with distilled water about 15 to 20 times to completely remove hydrofluoric acid, and finally soaking in 100% ethanol under UV light for 30 minutes to be sterilized. As a result, the coverslips on which host cells expressing the EGFR-mEos fusion protein and host cells expressing the PMT-mEos fusion protein were seeded were obtained.

1.4. Identification of Membrane Protein to which Ligand Did not Bind

The coverslip on which the cells were seeded as described in Example 1.3 was placed onto a microscope with a live cell chamber (37° C., 5% $CO_2$) and an electron multiplying charge coupled device (EM-CCD) and observed the cells at a single cell level. The microscope, the Olympus IX71 model, is designed based on total internal reflection fluorescence (TIRF), and can be used to observe only fluorescent molecules at a plasma membrane of a cell closely attached (within about 200 nm from a coverslip) to a round coverslip. mEos3.2 fluorescent proteins were randomly converted from a green form into a red from by cleaving their backbone using 405 nm laser, and an image of the randomly converted red-form mEos3.2 fluorescent protein was obtained by an electron multiplying charge coupled device (EM-CCD), ixon3 897, manufactured by Andor Technology, which can detect a signal emitted from a single fluorescent molecule using 561 nm laser.

The fluorescent images were sequentially obtained at regular intervals of time (about 150 ms), and a centroid was found from the signal of a single molecule present on each image through centroid fitting, and the moving distance per unit time and the trajectory of the fluorescent protein were determined by using multiple tracking between consecutive images, and a mean square displacement (MSD) was calculated by Equation 1.

FIG. 1 is a schematic diagram of a system that can specifically observe a target protein among many membrane proteins present in a cell membrane by labeling the target membrane protein with a fluorescent protein, under an environment in which binding of a ligand makes diffusion of the target protein slow.

FIG. 2 is a diagram illustrating a process of tracking the motion of a target membrane protein in a single cell attached to a round coverslip by TIRF and spatio-temporally averaging the tracking result to analyze the diffusion coefficient of the target membrane protein in a single cell. A ligand treatment gave a different environment in a single cell, and the trajectory of a single target membrane protein over time was acquired. To obtain statistical significance, the above procedures were repeated, and the values obtained therefrom were spatio-temporally averaged, thereby overcoming heterogeneity of the cell itself, and enabled to be compared with diffusion of the target membrane protein measured under different conditions.

1.5. Identification of Ligand-Bound Target Membrane Protein

Each group of the host cells expressing PMT-mEos3.2 and the host cells expressing EGFR-mEos3.2 obtained in Example 1.3 was treated with 20 μg/ml of cetuximab, and the changes of diffusion were observed before and after the treatment by the method described in Example 1.4. The results are shown in FIG. 3.

FIG. 3 illustrates randomly selected trajectories in the host cells expressing PMT-mEos3.2 and the host cells expressing EGFR-mEos3.2 before and after treatment with cetuximab, in which PMT has almost no change in length of the trajectory before and after the treatment with cetuximab, but EGFR shows an obviously shorter length of the trajectory after the treatment with cetuximab. Non-treatment (NT) shown in FIG. 3 represents a state in which nothing is applied to an external environment, and cetuximab represents the trajectories measured after the treatment with cetuximab. In each image, the enlarged image represents the trajectories of several fluorescent molecules randomly extracted from a corresponding region. It can be seen that in non-treated NT (left), both of the PMT and EGFR membrane proteins are relatively freely diffused.

However, it can be seen that, in the cetuximab (right), the motion patterns are different. Since PMT do not bind with cetuximab, there is no significant change in the length of the trajectory of the fluorescent molecule. However, since EGFR directly binds with cetuximab, it can be observed that the length of the trajectory of the fluorescent molecule becomes obviously shorter.

To prove that the result of the change shown in FIG. 3 is not caused by a certain factor generated during the experiment, but by EGFR and an antibody binding thereto, changes of other factors occurring before and after the treatment with cetuximab were observed. In each experiment, a total of 4,000 images were obtained, trajectories are obtained from these images, diffusion coefficients of PMT and EGFR were calculated by Equations 1 and 2, and then the mean and standard deviation of the diffusion coefficients are shown in FIG. 4.

FIG. 4 illustrates the means and standard deviations of diffusion coefficients of PMT and EGFR before and after the treatment with cetuximab for 10 cycles, and it can be seen from FIG. 4 that the diffusion coefficient of EGFR is changed by cetuximab, and not by other imaging factors during measurement.

FIG. 5 illustrates the quantitatively summarized results of FIG. 3, which show changes in diffusion coefficients (%) of PMT and EGFR after treatment with cetuximab, compared with the diffusion coefficients of non-treated PMT and EGFR. While PMT had almost no change in diffusion coefficient before and after the treatment with cetuximab, EGFR showed a change in diffusion coefficient of about 40% after the treatment with cetuximab. In detail, the diffusion coefficients may be obtained by Equations 1 and 2, and when a ratio of the change in diffusion coefficient is calculated by Equation 3, provided that diffusion coefficients obtained under different conditions were $D_{c1}$ and $D_{c2}$, PMT has almost the same $D_{c1}$ and $D_{c2}$ values, thereby having a very small change in diffusion coefficient, but the $D_{c2}$ value of EGFR is about 60% of the $D_{c1}$ value thereof, and thus it can be seen that the diffusion coefficient is reduced by about 40%.

As shown in FIGS. 1 to 5, an increase in size caused by the binding between the target membrane protein and the ligand leads to reduction in diffusion coefficient of the target membrane protein, and a degree of the reduction can be quantified. It could be confirmed that PMT that cannot bind to cetuximab had no significant change in diffusion coefficient before and after the treatment with cetuximab, but EGFR was reduced in diffusion coefficient after the treatment with cetuximab, and the reduction degree was about 40%.

Example 2. Measurement of Target Membrane Protein: GPCR 2.1 Plasmid for Preparing β2-AR-mEos3.2 Fusion Protein β2-AR (Addgene plasmid #14697) used in the experiment was provided by Dr. Robert Lefkowitz, and β2-AR DNA (SEQ ID NO: 6) was inserted into the pcDNA3.1/mEos3.2-his subcloned in Example 1.1 using restriction enzymes such as BamHI and XbaI, thereby constructing pcDNA3.1/β2-AR-mEos3.2-His.

2.2 Plasmid for Preparing FZD1-mEos3 Fusion Protein

FZD1 (Addgene plasmid #16819) used in the experiment was provided by Dr. Randall Moon, and FZD1 DNA (SEQ ID NO: 7) was inserted into the pcDNA3.1/mEos3.2-his subcloned in Example 1.1 using restriction enzymes such as BamHI and Xbal, thereby constructing pcDNA3.1/FZD1-mEos3.2-His.

2.3 Preparation of Host Cells for Expressing Fusion Protein

For an experiment to inactivate GPCR, COS7 cells were transfected with β2-AR-mEos3.2, FZD1-mEos3.2, and PMT-mEos3.2 (refer to Example 1.2) by the same method as described in Example 1.3, and each group of the transfected COS7 cells were starved in 1% serum (minimum condition)-containing medium for 16 hours. Also, for a pertussis toxin (PTX) experiment, prior to measurement of a membrane protein, each group of the transfected COS7 cells were treated with PTX at a concentration of 100 ng/ml for 6 hours.

2.4 Identification of Ligand-Bound Target Membrane Protein

Diffusion coefficients of PMT, FZD1 and β2-AR were measured by the same method described in Example 1.5, and the results are shown in FIGS. 7 and 8.

FIG. 6 illustrates that β2-AR basically do not bind with a Gi-protein, but as FZD1 bind with a Gi-protein, when treated with PTX, ADP of the Gi-protein is ribosylated, thereby inhibiting the binding with FZD1. According to the above-described mechanism, regardless of the presence of PTX, β2-AR has no change in diffusion coefficient, and FZD increases in diffusion coefficient after the treatment with PTX.

FIG. 7 illustrates changes in diffusion coefficients of PMT, FZD1, β2-AR before and after treatment with PTX.

FIG. 8 shows absolute values of mean diffusion coefficients of PMT, β2-AR, and EGFR, in which since β2-AR is faster than EGFR, the binding to β2-AR is more sensitively measured than EGFR.

As shown in FIGS. 7 and 8, the method can be even applied to GPCR without limitation to EGFR. This means that it can be applied to other membrane proteins, and also can detect intracellular binding as well as extracellular binding. Also, FIGS. 7 and 8 show that the method can detect the binding between EGFR and cetuximab, and the dissociation of FZD1 from the Gi-protein.

Example 3. Measurement of Target Membrane Protein in Different Environments

To prove technical reproducibility of the method described in Example 1, three groups of transfected COS7 cells were prepared on different days (batch#1, batch#2, and batch#3), two groups of transfected COS7 cells (batch#3-1 and batch#3-2) were prepared independently but on the same day, and then coverslips on which these batches were seeded were prepared. The host cells were treated with cetuximab by the same method as described in Example 1.4, and then a change in diffusion coefficient of EGFR was measured, and the results are shown in FIG. 9.

FIG. 9 illustrates the changes in diffusion coefficient of EGFR measured by the above-described method, in which batch#1, batch#2, and batch#3 represent the changes in diffusion coefficient of EGFR in the COS7 cells prepared in three different batches, and batch#3-1 and batch#3-2 represent changes in diffusion coefficient of EGFR measured at different glasses, but in the same batch.

As shown in FIG. 9, all of the batches prepared on different days and the batches independently prepared on the same day showed no difference in change in diffusion coefficient of EGFR, and it was confirmed by ANOVA analysis that there is no statistical difference between the batches (p=0.768).

Examples 4-6. Identification of Target Membrane Protein (Cell Lines: HEK293, HELA, and CHO-K1)

To demonstrate that target membrane proteins can be measured in other cell lines than COS7 cells, host cells expressing PMT-mEos3.2 and host cells expressing EGFR-mEos3.2 were prepared using HEK293, HELA, and CHO-K1 cells provided by ATCC instead of COS7 cells used in Example 1.3 by the method described in Example 1.4, and changes in diffusion coefficients of EGFR and PMT were measured by treating each group of the host cells with cetuximab by the method described in Example 1.5, and the results are shown in FIG. 10. The results obtained using HEK293, HELA, and CHO-K1 cells as host cells were described in Examples 4 to 6, respectively.

FIG. 10 illustrates changes in diffusion coefficient of EGFR in HEK293, HELA, and CHO-K1 by the above-described method, and like the results obtained with COS7 cells, in all cell lines, a reduced change in diffusion coefficient of EGFR caused by cetuximab was able to be measured.

Comparative Example 1. Measurement of Binding with Ligand: Western Blotting

As a comparative example to analyze the binding between a target membrane protein and a ligand, western blotting was carried out.

Ligand mAb 199.12 was purchased from Invitrogen, ligand mAb 528/mAb R-1 was purchased from Santa Cruz, anti-pEGFR (Y1068) antibody was purchased from Invitrogen, and anti-total EGFR and anti-pErk1/2 antibodies were purchased from Signaling, and an anti-actin antibody was purchased from MP biomedical.

COS7 cells were lysed with radioimmunoprecipitation (RIPA) buffer. The cell lysate was loaded in a 6 to 16% gradient SDS-PAGE gel to allow proteins to migrate in an electrical field. The proteins separated in the SDS-PAGE gel were transferred to a nitrocellulose membrane, treated with a primary antibody at 4° C. overnight, and then treated with a secondary antibody tagged with horseradish peroxidase (HRP) or IRDye800CW (Li-COR) at room temperature for 1 hour. The presence and amount of the proteins were detected using chemiluminescence (ECL system, Pierce) or infra-red fluorescence (Odyssey system, Li-COR), and the results are shown in FIG. 12.

FIG. 11 illustrates cetuximab, mAb 199.12, mAb 528 and mAb R-1 which can bind to EGFR at different sites.

FIG. 12 illustrates western blotting results, in which NT represents no treatment with an antibody, and EGF+/− represents treatment/non-treatment of EGF. As shown in FIG. 12, cetuximab and mAb 528 prevent phosphorylation of EGFR, and also prevent phosphorylation of Erk1/2 in a different manner, and mAb 199.12 and mAb R-1 do not effectively prevent the phosphorylation of EGFR. In detail, EGFR is activated by EGF, and pEGFR may be detected using an antibody that can specifically bind to the activated EGFR.

Since EGFR is not activated without EGF, it was not detected using pEGFR antibody, but in an EGF-existing environment, EGFR is activated by EGF, and the activated EGFR was detected using the pEGFR antibody, and therefore the same results as described are shown. pErk1/2 is a main marker to confirm downstream signaling during signal transduction, which maintains a minimal signal transduction in the EGF-free environment, and increases in the amount in the EGF-existing environment, and therefore it can be seen that the downstream signal transduction is effectively performed.

Actin is one of the main proteins composing a cell, which serves as a marker to confirm that a similar amount of proteins are used in each experiment when several western blotting analyzes are performed.

When EGF, and cetuximab or mAb 528 are present at the same time, EGF binding site on EGFR is interfered with cetuximab and mAb 528, and as a result, it inhibits the EGFR activation, whose tendency is seen through western blotting. However, mAb 199.12 and mAb R-1 do not show the tendency of inhibiting EGFR activation in the EGF-existing environment through the western blotting result, and thus it can be noted that mAb 199.12 and mAb R-1 do not have an influence on the EGFR activation caused by EGF.

Example 7. Measurement of Bonding with Ligand

The host cells expressing PMT-mEos3.2 and the host cells expressing EGFR-mEos3.2, which were obtained in Example 1.3, were treated with cetuximab, mAb 199.12, mAb 528, and mAb R-1, and diffusion coefficients were measured by the method described in Example 1.5. In detail, images were obtained in a non-treatment state (about 10 cycles), and after each type of the antibodies was mixed with the cell culture medium up to the final concentration of 20 μg/ml to induce binding of the antibody to a membrane protein present on the cell surface, images were obtained (about 10 cycles). Changes of diffusion coefficient before and after the host cells expressing PMT-mEos3.2 and the host cells expressing EGFR-mEos3.2 were treated with the corresponding antibodies were calculated by Equation 3, and the results are shown in FIG. 13.

FIG. 13 illustrates changes in diffusion coefficient, in which PMT do not specifically bind with cetuximab, mAb 199.12, mAb 528 and mAb R-1, and thus there is no change in diffusion coefficient before and after the treatment with the antibodies, but as EGFR specifically binds with all of cetuximab, mAb 199.12, mAb 528, and mAb R-1, the diffusion coefficient is changed by about 40% before and after the treatment.

As shown in FIG. 13, PMT has no change in diffusion coefficient before and after the treatment with the antibodies, but EGFR is changed in diffusion coefficient by about 40% before and after the treatment with the antibodies. This shows that the change in diffusion coefficient measured by the above-described method is influenced by direct binding, and is capable of being measured regardless of binding sites. These advantageous characteristics cannot be obtained using fluorescence resonance energy transfer (FRET) and protein fragment complementation assay (PCA).

Comparative Example 2. Molecular Specificity Distinction Test: Flow Cytometry

As a comparative example to analyze a molecular specificity distinction test between a target membrane protein and a ligand, flow cytometry was carried out.

Alexa Fluor 647 fluorescent molecules were conjugated to immunoglobulins (anti-Human (A21445)/anti-Mouse (A21235). Invitrogen), cetuximab, trastuzumab (Roche), and an anti-actin antibody ((691001), MP Biomedicals) to be employed for flow cytometry, and the flow cytometry was performed using Gallios manufactured by BD bioscience. In detail, COS7 cells were treated with the Alexa Fluor 647-conjugated antibody to induce binding with a membrane protein, and a fluorescent signal attached to the surface of the cell was observed by flow cytometry, and the results are shown in FIG. 15.

FIG. 14 illustrates cetuximab specifically binding to EGFR, and trastuzumab specifically binding to ErbB2.

FIG. 15 illustrates flow cytometry results, in which the x axis represents the intensity of a fluorescent signal, and the y axis represents a relative ratio of the cell populations having a specific level of intensity of a fluorescent signal. That is, as the graph goes to the right, the fluorescent signal becomes stronger, which is interpreted that more fluorescent dyes are attached to the cell surface.

As shown in FIG. 15, it can be seen that cetuximab or trastuzumab is relatively well attached to the cell surface (the immunoglobulin or actin serves as a control that does not specifically bind to a membrane protein present on the cell surface), but this approach cannot show to which membrane protein molecules cetuximab or trastuzumab binds. That is, the flow cytometry can reveal the presence or absence of a corresponding membrane protein using a fluorescent molecule-labeled antibody for each of EGFR and ErbB2 endogenously expressed in COS7 cells, but cannot reveal that, especially, cetuximab and trastuzumab specifically bind to EGFR and ErbB2, respectively.

Example 8. Molecular Specificity Distinction Test

Diffusion coefficients of PMT and EGFR were measured for the host cells expressing PMT-mEos3.2 and the host cells expressing EGFR-mEos3.2 obtained in Example 1.3 by the method described in Example 1.5, and in detail, each group of the host cells were treated with cetuximab, trastuzumab or an anti-actin antibody, and a change in diffusion coefficient was measured by Equation 3 using the values of the diffusion coefficients before and after the treatment with the antibody. The results are shown in FIG. 16.

FIG. 16 is a graph illustrating changes in diffusion coefficients before and after the host cells expressing PMT-mEos3.2 and the host cells expressing EGFR-mEos3.2 were treated with the cetuximab, trastuzumab, and anti-actin antibody, which were measured by the above-described method.

As shown in FIG. 16, when the diffusion coefficients of PMT and EGFR were measured by the above-described method, PMT had no change in diffusion coefficient by the treatment with the cetuximab, trastuzumab, or anti-actin antibody, but it was able to be seen that EGFR was changed in diffusion coefficient due to cetuximab. In detail, PMT has almost uniform diffusion coefficients regardless of the treatment of the antibodies as shown in the previous experimental results, and thus has a very small change in diffusion coefficient. However, since cetuximab specifically binds to EGFR, EGFR has a change in diffusion coefficient, but it does not show any changes in diffusion coefficient by trastuzumab and the anti-actin antibody which do not specifically bind to EGFR.

Compared to the flow cytometry results obtained in Comparative Example 2, the flow cytometry shows that cetuximab and trastuzumab bind to membrane proteins present on the cell surface, but cannot determine whether this binding is specific. However, when the diffusion coefficient is measured by the method of the present invention, it can be seen that EGFR is specifically bound with cetuximab, not trastuzumab.

Example 9. Sensitivity to Molecular Weight of Measuring Method of Target Membrane Protein When a target membrane protein binds with a ligand whose molecular weight is not exactly known, as well as the ligand whose molecular weight is known such as cetuximab, to prove that information about a molecular weight of the ligand which has not been known can be estimated from a degree of change in diffusion coefficient, materials having total four different molecular weights (17 kDa to 150 kDa) such as cetuximab (150 kDa), cetuximab Fab (50 kDa), cetuximab F(ab')$_2$ (90 kDa)) and an EGFR-specific binding aptamer (17 kDa) were bound with EGFR, and then an experiment of observing changes in diffusion coefficient of EGFR was performed.

Cetuximab was purchased from Merck Serono, cetuximab Fab and F(ab')2 were prepared using preparation kits (Pierce, 44685 and 44688), and the EGFR-specific binding aptamer was made using SELEX. As shown in Example 1.5, COS7 cells transfected with EGFR-mEos3.2 were treated with each of the four prepared ligands (cetuximab, cetuximab Fab, cetuximab F(ab')$_2$, and the EGFR-specific binding aptamer), and changes in diffusion coefficient of EGFR were measured before and after the treatment by the same method as described in Example 1.5, and the results are shown in FIGS. 18 and 19.

FIG. 17 is a diagram illustrating the bindings between the four different ligands with different molecular weights and EGFR, which are made at the same binding site.

FIG. 18 illustrates changes in diffusion coefficients of EGFR and PMT before and after the host cells expressing PMT-mEos3.2 and the host cells expressing EGFR-mEos3.2 were treated with cetuximab, cetuximab Fab, cetuximab F(ab')$_2$, and EGFR-specific binding aptamer.

FIG. 19 illustrates that the molecular weight of a ligand and the change in diffusion coefficient have a linear relationship.

As shown in FIGS. 17 and 19, it was confirmed that as the molecular weight of a ligand was increased as 17 kDa, 50 kDa, 90 kDa, and 150 kDa, the change in diffusion coefficient of EGFR was also increased by about 7%, 16%, 27%, and 38%, and it can be noted that such relationship is linear. In detail, when the diffusion coefficients were calculated by Equations 1 and 2, the molecular weight of a corresponding ligand can be estimated using the fact that the diffusion coefficient becomes smaller as the molecular weight of the ligand is increased.

Example 10. Measurement of Dissociation Constant 10.1 Measurement of Dissociation Constant of EGFR-WT When there is insufficient treatment with cetuximab, EGFRs are classified into two states: a cetuximab-bound EGFR state and an unbound EGFR state. If these two different EGFR states exist at the same time, a ratio of the two groups can be estimated by measuring a diffusion coefficient of EGFR by the method described in Example 1. Since the ligand-bound and unbound groups have different sizes, a difference between the diffusion coefficients of EGFR in these groups can be distinguished by the method described in Example 1, and therefore the dissociation constant between EGFR and cetuximab in a single living cell can be quantitatively measured using this ratio.

To demonstrate it, a diffusion coefficient of EGFR was measured in each environment in which the COS7 cells expressing EGFR-mEos3.2 prepared in Example 1.3 was treated with cetuximab at concentrations increased gradually from 0.02, 0.04, 0.08, 0.16, 0.32, 0.64 up to 1.28 µg/ml, which is the saturation level. The obtained diffusion coefficients of EGFR were converted into bound/unbound ratios between EGFR and cetuximab using Equations 4 to 8.

In the following Equations 4 to 8, U and B are random variables of a diffusion coefficient of ligand-unbound or ligand-bound target membrane proteins, respectively. For a simple model, it is assumed that there is no conversion between the two states, and the concentration of a ligand is represented as c.

$$M_{(C=c)} = \alpha_{(C=c)} * U + \beta_{(C=c)} * B \quad \text{[Equation 4]}$$

$M_{(C=c)}$ is the diffusion coefficient of a target membrane protein when the concentration of a ligand is c, $\alpha_{(C=c)}$ is the ratio of ligand-unbound membrane proteins to the total target membrane proteins, when the concentration of a ligand in one cell is c, and $\beta_{(C=c)}$ is the ratio of ligand-bound target membrane proteins to the total target membrane proteins, when the concentration of a ligand in one cell is c, and $\alpha_{(C=c)} + \beta_{(C=c)}$ is 1.

U is the diffusion coefficient of a ligand-unbound target membrane protein,

B is the diffusion coefficient of a ligand-bound target membrane protein.

$$E(M_{(C=c)}) = \alpha_{(C=c)} * E(U) + \beta_{(C=c)} * E(B) \quad \text{[Equation 5]}$$

$E(M_{(C=c)})$ is the mean diffusion coefficient of a target membrane protein when the concentration of a ligand is c, E(U) is the mean diffusion coefficient of a ligand-unbound target membrane protein, E(B) is the mean diffusion coefficient of a ligand-bound target membrane protein.

Therefore, the ratio of a ligand-bound membrane protein leads to the following Equation 6.

$$\beta_{(C=c)} = (E(M_{(C=c)}) - E(M_{(C=0)}))/(E(M_{(C=s)}) - E(M_{(C=0)})) = (D_{(C=c)} - D_{(C=0)})/(D_{(C=s)} - D_{(C=0)})$$

$$E(U) = E(M_{(C=0)}), E(B) = E(M_{(C=s)}) \quad \text{[Equation 6]}$$

$D_{(C=c)}$ is the diffusion coefficient of a target membrane protein when the ligand concentration in one cell is c. Therefore, the dissociation constant ($K_d$) is defined as Equation 7.

$$K_d = ([L][R])/([RL]) = (c * \alpha_{(C=c)})/\beta_{(C=c)} \quad \text{[Equation 7]}$$

[L] is the concentration of a ligand,

[R] is the concentration of a target membrane protein (receptor),

[LR] is the concentration of the binding complex of a ligand and a target membrane protein.

Equation 8 may be obtained by Equations 6 and 7.

$$(D_{(C=c)} - D_{(C=0)})/(D_{(C=s)} - D_{(C=0)}) = c/(K_d + c) \quad \text{[Equation 8]}$$

Cooperativity as well as a dissociation constant between EGFR and cetuximab was confirmed by Equations 4 to 8 from the bound/unbound ratio between EGFR and cetuximab at a single cell level. In addition, it was confirmed that the dissociation constant measured as described above and the cooperativity values obtained from a scatchard plot were similar to those obtained by an actual experiment carried out in vitro, and the detail results are shown in FIGS. 20 to 22.

FIG. 20 is a diagram illustrating that cetuximab binding to EGFR increases in number as the concentration of cetuximab is increased.

FIG. 21 illustrates the reduction of a diffusion coefficient of EGFR as the concentration of cetuximab in a single one cell is increased from 0.02 to 1.28 µg/ml. A reduced value of the diffusion coefficient of EGFR was normalized by the value in non-treatment condition.

FIG. 22 is a graph illustrating a ratio of cetuximab binding to EGFR as the concentration of cetuximab is increased based on the result of FIG. 21, and thereby the dissociation constant between EGFR and cetuximab can be calculated. Also, the inner graph of FIG. 22 shows that there is no cooperativity in the binding of cetuximab according to the scatchard plot.

As shown in FIGS. 20 to 22, when the diffusion coefficient of EGFR was measured by the above-described method, the size of the ligand-bound or ligand-unbound group is not the same as each other, and therefore a difference between the diffusion coefficients of EGFR can be distinguished by the degree of binding between EGFR and cetuximab, and it can be confirmed that the dissociation constant between EGFR and cetuximab in a single living cell can be quantitatively measured using this ratio.

10.2 Measurement of Dissociation Constant of Mutant Form, EGFRvIII

The binding between a ligand and a fluorescence-labeled target membrane protein can only be observed by the method described in Example 1. In other words, even in an environment in which a variety of membrane proteins are mixed, only the fluorescence-labeled target membrane protein can be observed.

To demonstrate this, an experiment was performed by a method of treating EGFRvIII (SEQ ID NO: 8), which is a mutant form of EGFR from which a part of an extracellular domain is deleted, compared to EGFR, with cetuximab and mAb R-1 antibody. In detail, transfected cells were prepared by the method described in Example 1, except that, instead of EGFR-mEos3.2, EGFRvIII-mEos3.2 was expressed in COS7 cells, and PMT-expressed COS7 cells were prepared by the same method as used above. Also, the experiment was performed with mAb R-1 that binds to EGFR but does not bind to EGFRvIII by the same method as described in Example 10.1, and the results are shown in FIG. 24.

FIG. 23 illustrates that EGFR WT can bind to both cetuximab and the mAb R-1 antibody, but the mutant form, EGFRvIII, only binds with cetuximab, not mAb R-1. FIG. 24 illustrates that since PMT does not have the binding of two antibodies such as cetuximab and mAb R-1, a reduced diffusion coefficient of PMT is not shown, but EGFRvIII binds with cetuximab, but not with mAb R-1.

As shown in FIG. 24, it can be confirmed that a reduced diffusion coefficient of EGFRvIII due to cetuximab is obvious, but reduced diffusion coefficient of EGFRvIII due to mAb R-1 is insignificant. This means that EGFR vIII, which is a mutant made by deleting a mAb R-1 binding site from EGFR WT, binds to cetuximab, but not to mAb R-1.

The dissociation constant between EGFR vIII and cetuximab was measured by a dose-dependent test, and in detail, the diffusion coefficient of EGFRvIII was measured by the method described in Example 1.4 while the concentration of cetuximab was increased as 0.02, 0.04, 0.08, 0.16, 0.32, 0.64, 1.28 µg/ml by the same method as described in Example 1.4, the dissociation constant between EGFRvIII and cetuximab was measured as described in Example 10.1 using the ratio of binding with cetuximab and analyzed by plotting a scatchard plot, and then the results are shown in FIG. 25.

FIG. 25 illustrates the dissociation constant and cooperativity between EGFRvIII and cetuximab using the method described in Example 10.1. As shown in FIG. 25, it was able to be confirmed from the scatchard plot that there is no cooperativity in the binding between EGFRvIII and cetuximab.

As shown in FIGS. 20 to 25, the method can obtain the dissociation constant and cooperativity of a ligand specifically binding to a target membrane protein to be observed in a live cell.

Example 11. Analysis of Process of Forming Complex of Target Membrane Protein

When the diffusion coefficients of target membrane proteins including EGFR are measured by the method described in Example 1, the size of a molecule becomes larger during the formation of a complex of the target membrane proteins, and is directly connected to the diffusion coefficient. Therefore, the process of forming the complex may be known based on the diffusion coefficient.

Host cells expressing EGFR-mEos3.2 prepared in Example 1.3 were treated with cetuximab, a secondary antibody (goat anti-human immunoglobulin (IgG) antibody (81-7100), invitrogen) and a tertiary antibody (rabbit anti-goat immunoglobulin (A10537), invitrogen) in turn, and in order to figure out the process of forming the complex, the cetuximab, secondary antibody and tertiary antibody that sequentially bind to EGFR as shown in FIG. 26 are treated in turn to measure the diffusion coefficient of EGFR by the method described in Example 1.5. The results are shown in FIG. 27.

FIG. 26 illustrates sequentially binding of the cetuximab, secondary antibody and tertiary antibody to the host cells expressing EGFR-mEos3.2, and FIG. 27 illustrates the diffusion coefficients of EGFR measured in the order of treating the host cells expressing EGFR-mEos3.2 with the cetuximab, secondary antibody and tertiary antibody.

As shown in FIG. 27, when the host cells expressing EGFR-mEos3.2 were sequentially treated with the cetuximab, secondary antibody and tertiary antibody, the diffusion coefficients of EGFR also tended to be reduced in the same order. The size of the final complex formed by binding the cetuximab, secondary antibody and tertiary antibody to the target membrane protein was about 600 kDa or more, and the reduction of the diffusion coefficient of EGFR caused by binding the tertiary antibody to the cetuximab and secondary antibody complex was about 12%. As a result, it can be seen that such a complex forming process can also be applied to a larger complex having a size of 600 kDa or more.

Contrarily, diffusion coefficients of EGFR were measured by sequentially treating the host cells expressing EGFR-mEos3.2 with the cetuximab, tertiary antibody and secondary antibody by the same method as described in Example 1.5, and the results are shown in FIG. 28.

FIG. 28 illustrates the diffusion coefficients of EGFR measured by sequentially treating EGFR with the cetuximab, secondary antibody and tertiary antibody.

As shown in FIG. 28, when the EGFR was sequentially treated with the cetuximab, tertiary antibody and secondary antibody, a complex was formed as soon as the secondary antibody binds to it, and therefore at this moment, a dramatic change in diffusion coefficient of EGFR, for example, about 30%, was shown.

Comparing FIGS. 27 and 28, when EGFR was treated with the cetuximab and then the tertiary antibody, the diffusion coefficient of EGFR was not changed, but the secondary antibody first bound with the tertiary antibody, and then bound with the cetuximab, and therefore a much larger reduction in diffusion coefficient of EGFR was shown. Such specificity shows that the above-described method may become an effective means to study the process of forming the complex of target membrane proteins.

Example 12. Observation of Target Endogenous Membrane Protein: Endogenous EGFR Expressed in COS7 Cells EGFR-specific binding was observed using a mouse (monoclonal) Anti-Human Epidermal Growth Factor Receptor (mAb 199.12 (Invitrogen)) among various types of antibodies targeting EGFR. A target protein may be regulated by antibody binding, but mAb 199.12 is known as an antibody insignificantly affecting the activity of EGFR.

12.1 Preparation of Fab Fragment

Fab fragments were generated using a Fab preparation kit (Pierce, 44685). First, a resin conjugated with a proteinase, papain, was mixed with an immunoglobulin antibody in a buffer effective for an enzyme reaction to occur and the reaction was conducted at 37° C. for 5 to 6 hours. After the reaction was completed, the antibody that is cleaved into two Fab fragments and an Fc fragment and the papain resin were centrifuged to separate only a supernatant. A protein A-conjugated resin and the supernatant were mixed, and then centrifuged again, thereby obtaining a purified Fab fragment.

12.2 Binding Between Antibody and Organic Fluorescent Dye

Antibodies were conjugated with an organic fluorescent dye, Alexa Fluor 647, using an Alexa Fluor® 647 antibody labeling kit (Invitrogen). The antibodies were added in a 0.1M sodium bicarbonate solution, and mixed with a fluorescent dye to which functional groups such as a succinimidyl ester or tetrafluorophenyl ester was tagged to allow a reaction for 1 hour, thereby forming a stable complex between the fluorescent dye and a primary amine group in the antibody. It were loaded on a purifying resin to bind remaining non-binding fluorescent dyes to the resin, and then centrifuged to obtain a supernatant, from which only the antibodies conjugated with the fluorescent dyes were isolated.

12.3 Preparation of Coverslip and Cell Seeding

Intact cells without any treatment were seeded on a 25-mm or 18-mm-diameter coverslip. These coverslips were prepared by procedures of sonication in acetone at 42° C. for 30 minutes to minimize autofluorescence of the coverslip, washing with distilled water three times, sonication again in 1% hydrofluoric acid at 42° C. for 10 minutes, washing with distilled water about 15 to 20 times to completely remove hydrofluoric acid, and finally soaking in 100% ethanol and exposure to UV light for 30 minutes to sterilize.

When the cells were seeded onto the prepared coverslip, the coverslip was treated with a surface coating material to facilitate cells to be attached to the coverslip. As the surface coating material that can be used herein, collagen, fibronectin, gelatin or poly-L-lysine may be used.

12.4 Fixation of the Cell-Seeded Coverslip onto Microscope

The coverslip on which cells were seeded as described in Example 12.3 was placed onto a microscope with a live cell chamber (37 C, 5% $CO_2$) and an electron multiplying charge coupled device (EM-CCD) to observe the cells at a single cell level. The microscope, Olympus IX71 model, is designed based on total internal reflection fluorescence (TIRF), and therefore can observe only fluorescent molecules at a plasma membrane of a cell closely attached (within about 200 nm from a coverslip) to the round coverslip.

12.5 Treatment with Organic Fluorescent Dye-Binding Antibody

Endogenous membrane proteins expressed in the cells seeded as described in Example 12.4 were specifically labeled with fluorescent dye-conjugated Fabs prepared in Examples 12.1 and 12.2. A degree of labeling the target proteins may be regulated by changing the concentration and treatment time of the fluorescent dye-conjugated Fab.

After the endogenous protein was sufficiently labeled, unbound fluorescent dye-conjugated Fabs present in the solution were removed by washing with a growth medium 2 to 3 times.

To induce photoswitching and inhibit photobleaching of an organic fluorescent dye under the condition in which cells were alive, 1 mM β-mercaptoethylamine (MEA), 0.2 u/ml protocatechuic acid (PCA) and 2.5 mM protocatechuate-3, 4-dioxygenase (PCD) were added to a cell culture medium.

12.6 Observation of Endogenous Membrane Protein to which Ligand and Interaction Partner Did not Bind The fluorescence-labeled endogenous EGFR prepared in Example 12.5 was illuminated with 642 nm laser to temporarily turn off the fluorescence of Alexa Fluor 647 to make it possible to observe at a single molecule level, the electron state of the fluorescent molecule was changed with 405 nm laser to allow to randomly turn on the fluorescence, and then fluorescent images were sequentially obtained with 642 nm laser at regular intervals of time (about 50 ms) by an electron multiplying charge coupled device (EM-CCD) ixon3 897, manufactured by Andor Technology, which can detect a signal transmitted from a single fluorescent molecule. A signal of the single molecule present on each image was found, and then the images were compared to each other, thereby tracking and measuring the moving distance and trajectory of the fluorescent protein per unit time, and a mean square displacement (MSD) was calculated by Equation 1.

FIG. 29 illustrates a process of detecting endogenous EGFR by conjugating the photoswitchable fluorescent organic dye, Alexa Fluor 647, to the Fab fragment that can specifically bind to the endogenous EGFR (left). This can be observed because, actually, Alexa Fluor 647 is photoactivated when binding to EGFR of a cell and emits a fluorescent signal as shown in the middle image. As the position information and trajectory of the fluorescent signal emitted from each single molecule are tracked down until the fluorescent signal is photobleached, a diffusion coefficient may be obtained. The right image illustrates the trajectories of tracked 10,000 single molecules.

12.7 Observation of Endogenous Membrane Protein to which Ligand and Interaction Partner Bind The cells in which the endogenous EGFR was labeled with the fluorescent dye, prepared in Example 12.5, were treated with 20 μg/ml of cetuximab. As shown in FIG. 30, it was confirmed that fluorescent dye-conjugated mAb 199.12 and cetuximab have different EGFR-specific binding sites, they do not affect each other. The cells before and after treatment with cetuximab were observed by the method described in Example 12.6, diffusion coefficients before and after the treatment were calculated by Equations 1 and 2, and means and standard deviations thereof are shown in FIG. 31.

FIG. 30 illustrates the result of confirming that the bindings of mAb 199.12 and cetuximab to the endogenous EGFRs are not influenced by each other. 1 µg/ml each of cetuximab and mAb 199.12 antibody, which were labeled with a fluorescent dye, and 100 µg/ml of cetuximab, which was not labeled with a fluorescent dye, were mixed to allow binding to the endogenous EGFR expressed in the COS7 cells for 30 minutes, and a fluorescent signal depending on a binding degree was detected by flow cytometry. The flow cytometry results show that the binding degree of the mAb 199.12 antibody is not interfered even with the 100-fold higher concentration cetuximab, but the binding of the cetuximab antibody is inhibited by the high concentration of cetuximab to which a fluorescent dye is not conjugated, and therefore a reduced fluorescent signal was detected.

FIG. 31 illustrates data obtained by observing a specific binding aspect between the endogenous EGFR and cetuximab. Fab of the mAb 199.12 antibody specifically binding to EGFR was purified, labeled with Alexa Fluor 647 fluorescent dye, and then added to a single living COS7 cell to bind to the endogenous EGFR expressed in the cell. A diffusion coefficient was obtained before the treatment with an immunoglobulin antibody and cetuximab, and a diffusion coefficient changed by the binding between the EGFR and the immunoglobulin antibody or cetuximab was calculated after the treatment with the immunoglobulin antibody and cetuximab. It can be observed that, since the immunoglobulin antibody does not specifically bind to EGFR, there is almost no change in diffusion coefficient, but since cetuximab specifically binds to EGFR, the diffusion coefficient is changed by about 40%.

12.8 Identification of Endogenous EGFRs Expressed in Various Cell Lines

To observe the change in diffusion coefficient of endogenous EGFRs expressed in various cell lines by cetuximab, COS7, A431, MDA-MB-231, BT20, HCC827 cell lines were prepared as described in Example 12.4, endogenous EGFRs expressed in the cells were labeled with fluorescent dye using Fab fragments as described in Example 12.5, and a diffusion coefficient under a non-treatment condition was measured as described in Example 12.6. Afterward, the same cells as previously used were treated with an immunoglobulin antibody or cetuximab, and diffusion coefficients were measured by the same method as described above. Changes in diffusion coefficient were calculated by Equation 3, compared to that under the non-treatment condition, and the results are shown in FIG. 32.

FIG. 32 illustrates the quantitative results of means and standard deviations of diffusion coefficients changed by the immunoglobulin antibody and cetuximab binding to five different cell lines. Compared with the diffusion coefficient of the endogenous EGFR in each cell under the non-treatment condition, there were almost no changes in diffusion coefficient before and after the immunoglobulin antibody was treated, but after the treatment with cetuximab, all cells were changed in diffusion coefficient by about 40%. Specifically, the diffusion coefficients may be obtained by Equations 1 and 2, and provided that the diffusion coefficients under different conditions are $D_{c1}$ and $D_{c2}$, a ratio of the change in diffusion coefficient is calculated by Equation 3. With the treatment of the immunoglobulin antibody, $D_{c1}$ and $D_{c2}$ values are almost the same, which means that the change in diffusion coefficient is very small. However, with the treatment of the cetuximab, $D_{c2}$ value is about 60% of $D_{c1}$ value, which means that the diffusion coefficient is reduced by about 40%.

Example 13. Observation of Endogenous Membrane Protein in Primary Cell Originating from Animal Model: Observation of Endogenous EGFRs in Various Types of Primary Cells Isolated from Mouse's Lung 13.1 Preparation of Cell Marker-Specific Antibody to which Fluorescent Dye is Conjugated Since, unlike a cell line, cells purified from tissues include a mixture of various types of cells, cells were labeled with primary antibodies specific to various cell membrane markers (Sca-1, PECAM) and fluorescent dye-conjugated secondary antibodies binding to the primary antibodies to determine the type of a cell to be observed. Here, to enable observation using lasers with different wavelengths, a type of the fluorescent marker was different depending on the marker (Pacific blue, Alexa Fluor 488, Dylight 549).

13.2 Purification of Primary Cells from Mouse's Lung Tissues and Cell Seeding

A mixed liquid of 0.5 mg/ml Collagenase type II (Worthington) and 1 mg/ml Collagenase type IV (Worthington) was injected into a lung tissue of a 8-week-old C57BL/6 mouse model through a respiratory tract to dissolve the tissue, and the separated lung tissue was put into a collagenase mixed liquid at 37° C. for 30 minutes. After neutralization of collagenase using PBS, and the tissue sample was centrifuged to obtain only cells, which was strained with a cell strainer (BD falcon) to separate single cells. The separated cells were grown in a growth medium treated with a fibroblast growth inhibitor for 24 hours, and seeded on an 18-mm-diameter coverslip and fixed on a microscope by the methods described in Examples 12.3 and 12.4.

13.3 Classification of Primary Cells by Cell Labeling

The fixed primary cells of murine lung were treated with a pacific blue fluorescent dye-conjugated antibody against Sca-1 protein (Invitrogen), a Dylight 549-conjugated secondary antibody which binds to primary antibody against Pecam protein (Santa cruz), and an Alexa Fluor 647 fluorescent dye-conjugated anti-EGFR protein antibody. Using lasers with different wavelengths suitable for respective fluorescent dyes (405, 488, 561, and 633 nm), the autofluorescence level, protein expression level and motion of each protein were observed by the method described in Example 12.6. Based on the results, compared with markers for the previously known types of cells in the lung cell tissue (Carla F. Bender Kim, et al., Cell, Vol. 121, 823-835, Jun. 17, 2005), four different types of cells that are mixed in lung cell groups separated from one mouse model were classified, and then a diffusion coefficient of endogenous EGFR in each cell type was measured, and a change in diffusion coefficient by cetuximab was measured.

FIG. 33 illustrates images of the mouse primary cells classified by markers for the cell types in the lung cell tissue and autofluorescence levels. DIC is an image showing an original cell shape, and all of Sca-1, Pecam and autofluorescence are fluorescent images. Cell#1 in which Sca-1 was very highly expressed and Pecam was rarely expressed was classified as a Bronchio-alveolar stem cell (BASC), and cell#2 in which all of Sca-1 and Pecam were expressed was able to be classified as an endothelial cell. Cell#3 showed very low expression of Sca-1 and Pecam but very high autofluorescence at a 488 nm channel, and therefore it is considered as an AT2 cell, and cell#4 in which Sca-1 and Pecam were rarely expressed and the autofluorescence level was very low is considered as a Clara cell.

FIG. 34 illustrates the results of observing changes in diffusion coefficient depending on patterns of binding cetuximab to endogenous EGFRs expressed in the four types of the cells classified in FIG. 33, such as the BASC, endothelial cell, AT2, and Clara cells. It was seen that the EGFRs expressed in the BASC cell and the Clara cell show a great change in diffusion coefficient due to cetuximab, for example, by about 40%, but the endothelial cell and the AT2 cell show the change in diffusion coefficient by less than 10%.

It would be understood by those of ordinary skill in the art that the above descriptions of the present invention are exemplary, and the exemplary embodiments disclosed herein can be easily modified into other specific forms without changing the technical spirit or essential features of the present invention. Therefore, it should be interpreted that the exemplary embodiments described above are exemplary in all aspects, and are not limitative.

The invention claimed is:

1. A method of analyzing a binding aspect between a candidate material and a target membrane protein in a living cell, the method comprising:
obtaining diffusion coefficients of the target membrane protein before and after treatment with the candidate material in the living cell expressing the target membrane protein, and analyzing a change in diffusion coefficient of the target membrane protein obtained thereby.

2. The method of claim 1, wherein the analysis of the binding aspect between the target membrane protein and the candidate material includes the analysis of binding between the target membrane protein and the candidate material, a ratio of target membrane proteins that the candidate material binds to among the total target membrane proteins, a molecular weight of the candidate material bound to the target membrane protein, a dissociation constant between the target membrane protein and the candidate material, or a process of forming a complex between the target membrane protein and the candidate material.

3. The method of claim 1, wherein the target membrane protein is selected from the group consisting of an integral membrane protein, a peripheral membrane protein, a transmembrane protein, a membrane glycoprotein and a lipid anchored membrane protein.

4. The method of claim 1, wherein the candidate material includes at least one selected from the group consisting of a compound, a nucleic acid, a saccharide, a carbohydrate, a lipid, a peptide, and a protein.

5. The method of claim 1, wherein the diffusion coefficient of the target membrane protein is obtained by detecting the motion of the membrane protein in a cell membrane by single particle tracking (SPT).

6. The method of claim 5, wherein the diffusion coefficient is obtained by Equations 1 and 2:

$$MSD(\Delta) = \frac{1}{N-\Delta} \sum_{n=1}^{N-\Delta} ((x_{n+\Delta} - x_n)^2 + (y_{n+\Delta} - y_n)^2) \quad \text{[Equation 1]}$$

where $\Delta$ is the step size between coordinates of the target membrane protein particle, wherein $\Delta$ is a positive integer, $MSD(\Delta)$ is the mean square displacement of a target membrane protein particle with respect to the step size between coordinates of the target membrane protein particle, N is the total number of a pair of coordinates in one trajectory for the target membrane protein particle, $(x_n, y_n)$ are the coordinates of the target membrane protein particle at an $n^{th}$-numbered position in one trajectory, $(x_1, y_1)$ are the coordinates of the target membrane protein particle at the start point in one trajectory, $(x_N, y_N)$ are the coordinates of the target membrane protein particle at the end point in one trajectory, and $(x_{n+\Delta}, y_{n+\Delta})$ are the coordinates of the target membrane protein particle at an n+Δ-numbered position in one trajectory, however, n+Δ is the same as or smaller than N; and MSD(Δ)=4DΔ [Equation 2]

where D is the diffusion coefficient, and Δ is the step size between coordinates of the target membrane protein particle.

7. The method of claim 1, wherein the change in the diffusion coefficient is obtained by Equation 3:

Change in diffusion coefficient (%)=100*|1−($D_{c2}$/$D_{c1}$)| [Equation 3]

where $D_{c1}$ is the diffusion coefficient of the target membrane protein at a concentration c1 of the candidate material in a peripheral environment of the cell at a single cell level, and $D_{c2}$ is the diffusion coefficient of the target membrane protein at a concentration c2 of the candidate material in a peripheral environment of the cell at a single cell level.

8. The method of claim 7, wherein, when the change in the diffusion coefficient (%) obtained by Equation 3 is 5% or more, the candidate material is determined as a ligand binding to the target membrane protein.

9. The method of claim 5, wherein the detection of the movement of the membrane protein in the cell membrane is performed by detecting fluorescence signal of a fluorescent protein in a cell expressing a fusion protein of the target membrane protein and the fluorescent protein.

10. The method of claim 9, wherein the fluorescent protein includes one or more selected from the group consisting of a green fluorescent protein (GFP) type, a blue fluorescent protein (BFP) type, a cyan type, a yellow fluorescent protein (YFP) type, a red fluorescent protein (RFP) type, an orange type, a far-red type, a near-IR, a photoactivatable protein, a photoconvertible protein, and a photoswitchable protein.

11. The method of claim 9, wherein the fluorescent protein includes one or more selected from enhanced green fluorescent protein (EGFP), Emerald, Superfolder GFP, azami green mWasabi, TagGFP, AcGFP, T-sapphire, mUKG, Clover, mNeonGreen, enhanced blue fluorescent protein (EBFP), EBFP2, Azurite, mTagBFP, mKalama1, Sirius, enhanced cyan fluorescent protein (ECFP), monomeric ECFP (mECFP), Cerulean, mTurquoise, mTurquoise2, CyPet, TagCFP, mTFP1 (Teal), SCFP3A, monomeric Midoriishi Cyan, enhanced yellow fluorescent protein (EYFP), Topaz, Benus, mCitrine, YPet, TagYFP, PhiYFP, mBanana, SYFP2, mRuby, mRuby2, mApple, mStrawberry, mRFP1, mCherry, mRaspberry, dKeima-Tandem (monomeric version), HcRed-Tandem (monomeric version), mPlum, mKate2, mNeptune, mKate2, mNeptune, TagRFP657, IFP1.4, PA-GFP, PAmCherry1, PaTagRFP, PS-CFP2, mEos2, mEos3.2, PSmOrange and Dronpa.

12. The method of claim 1, wherein the cell expressing the fusion protein of the target membrane protein and the fluorescent protein is selected from the group consisting of a human embryonic kidney (HEK) cell, HEK 293 cell, 3T3-L1 cell, C6 cell, Chinese hamster ovary (CHO) cell, CHOK1 cell, NIH/3T3 cell, baby hamster kidney (BHK) cell, COS1 cell, COS7 cell, HaCaT cell, HeLa cell, HeLa S3 cell, HepG2 cell, HL-60 cell, HUV-EC-C cell, Jurkat cell, K-562 cell, L6 cell, MCF7 cell, MDCK cell, NIH/3T3 cell, RAW 264.7 cell, RBL-1 cell, SH-SY5Y cell and U-937 cell.

13. The method of claim 5, wherein the detection of the movement of the membrane protein in the cell membrane is performed with a fluorescent material-conjugated probe specifically binding to the target membrane protein.

14. The method of claim 13, wherein the probe is an antibody, an aptamer, or a non-antibody protein scaffold.

15. The method of claim 13, wherein the fluorescent material is an organic fluorescent dye.

16. The method of claim 15, wherein the organic fluorescent dye is selected from Atto 488, Alexa Flour 488, Dy505, Rhodamine 123, Atto 520, Dy 530, ATTO 532, Alexa Fluor 532, Fluorescein, FITC, Cy2, Cy3B, Alexa Flour 568, TAMRA, Cy3, Cy3.5, SNAP-Cell TMR-Star, Atto 565, Atto 590, Alexa Fluor 647, Cy5, Atto 647, Atto 647N, Dyomics 654, Atto 655, TMP-ATTO 655, Atto 680, Cy5.5, Atto 680, Alexa Fluor 680, Atto 700, Alexa Fluor 700, DyLight 750, Cy7, Alexa Flour 750, Atto 740, Alexa Flour 790, and IRDye 800 CW.

17. The method of claim 1, further comprising:
measuring the diffusion coefficient of the target membrane protein after the treatment with the candidate material at several time points, and analyzing a change in a diffusion coefficient of at least one target membrane protein obtained thereby over time.

18. The method of claim 17, further comprising:
determining membrane protein-specific endocytosis by analyzing the change in the diffusion coefficient of the target membrane protein over time.

19. The method of claim 1, wherein the candidate material is a drug.

* * * * *